United States Patent [19]

Abrahmsen et al.

[11] Patent Number: 5,736,512
[45] Date of Patent: Apr. 7, 1998

[54] SERINE PROTEASE VARIANTS HAVING PEPTIDE LIGASE ACTIVITY

[75] Inventors: Lars Abrahmsen, Stockholm, Sweden; John Burnier, Pacifica, Calif.; James A. Wells, Burlingame, Calif.; David T. Jackson, San Mateo, Calif.

[73] Assignee: Genentech, Inc., South San Francisco, Calif.

[21] Appl. No.: 475,640

[22] Filed: Jun. 7, 1995

Related U.S. Application Data

[62] Division of Ser. No. 386,000, Feb. 9, 1995, Pat. No. 5,629,173, which is a division of Ser. No. 218,873, Mar. 28, 1994, abandoned, which is a continuation of Ser. No. 13,445, Feb. 4, 1993, abandoned, which is a continuation-in-part of PCT/US91/05480 filed on Aug. 6, 1991, which is a continuation-in-part of Ser. No. 566,026, Aug. 9, 1990, abandoned.

[51] Int. Cl.$^6$ .............. A61K 38/00; C12P 21/06; C07K 1/17
[52] U.S. Cl. .............. 514/12; 435/68.1; 435/212; 435/213; 435/214; 435/215; 435/216; 435/217; 435/218; 435/219; 435/220; 435/221; 435/222; 435/223; 435/224; 435/225; 435/226; 530/338; 530/345; 530/409; 530/410
[58] Field of Search .............. 435/68.1, 212–226; 530/345, 338, 409, 410; 514/12

[56] References Cited

U.S. PATENT DOCUMENTS

| | | |
|---|---|---|
| 2,362,511 | 11/1944 | Teeters .............. 260/78 |
| 4,760,025 | 7/1988 | Estell et al. . |
| 4,801,739 | 1/1989 | Franz et al. .............. 560/179 |
| 5,155,033 | 10/1992 | Estell et al. . |
| 5,403,737 | 4/1995 | Abrahmsen et al. .............. 435/252.3 |
| 5,464,739 | 11/1995 | Johnson et al. .............. 436/903 |
| 5,629,173 | 5/1997 | Abrahmsen et al. .............. 435/68.1 |

FOREIGN PATENT DOCUMENTS

WO92/02615  2/1992  WIPO .

OTHER PUBLICATIONS

Caldwell, R., et al., "Analysis of the Catalytic Importance of a Helix Dipole in Subtilisin Using Site–Directed Mutagenesis", *American Chemical Society Abstract MBTD–73*, Sep. 10–15, 1989.

Carter, P., et al., "Dissecting the Catalytic Triad of a Serine Protease", *Nature*, 332 (7):564–568 (1988).

Abrahmsen, L., et al., "Engineering Subtilisin and Its Substrates for Efficient Ligation of Peptide Bonds in Aqueous Solution", *Biochemistry*, 30:4151–4159 (1991).

Primary Examiner—Jerry D. Johnson
Attorney, Agent, or Firm—Flehr Hohbach Test Albritton & Herbert LLP; Richard F. Trecartin

[57] ABSTRACT

The invention relates to serine protease variants derived from precursor serine proteases via recombinant and/or chemical methods to form protease variants having improved peptide ligase activity. The invention also includes novel ligation substrates which in combination with the serine protease variants and a second ligation substrate are capable of forming a ligation product. The invention also relates to methods for forming such ligation products and the products formed thereby.

12 Claims, 16 Drawing Sheets

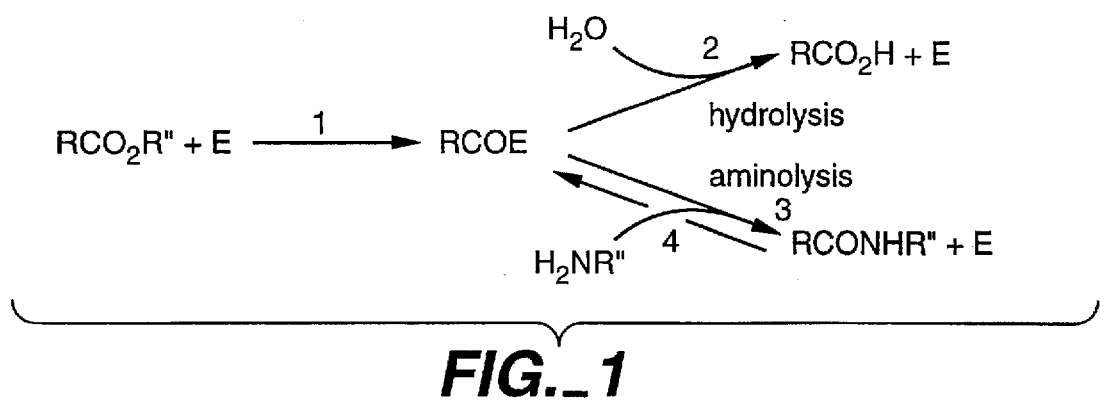
FIG._1
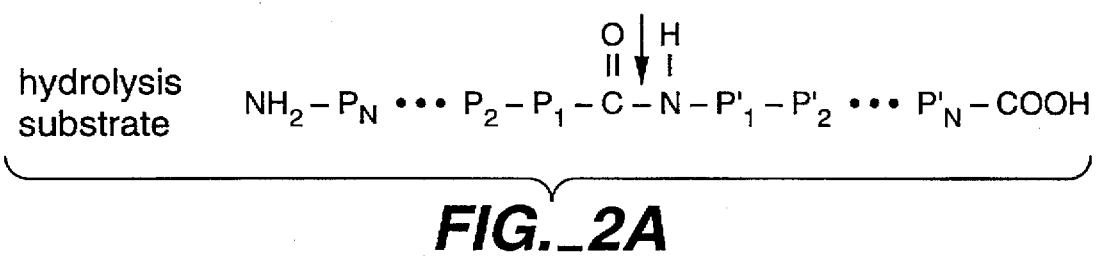
FIG._2A
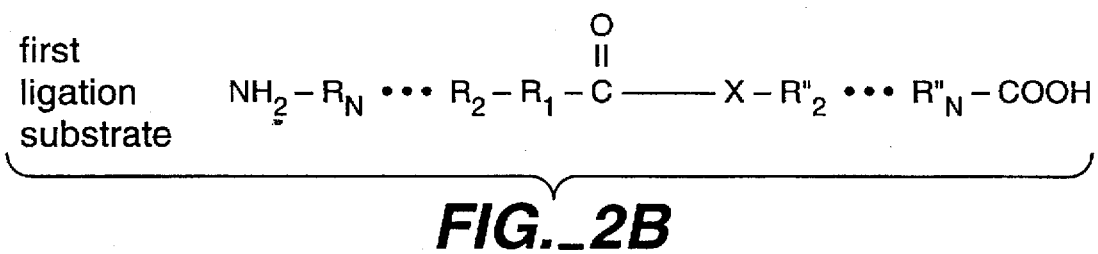
FIG._2B
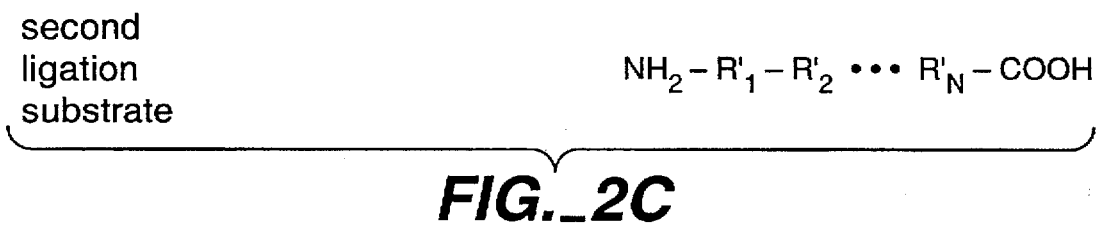
FIG._2C
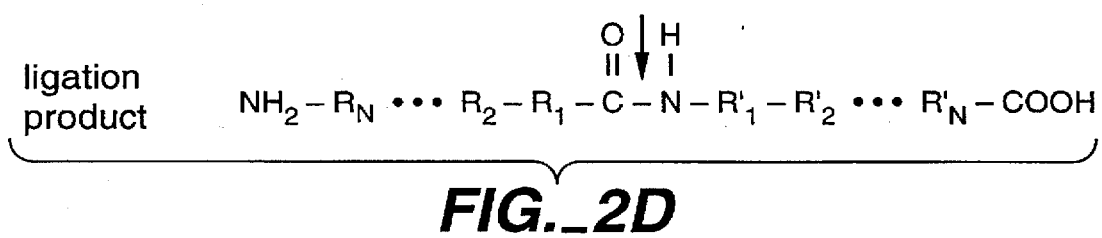
FIG._2D

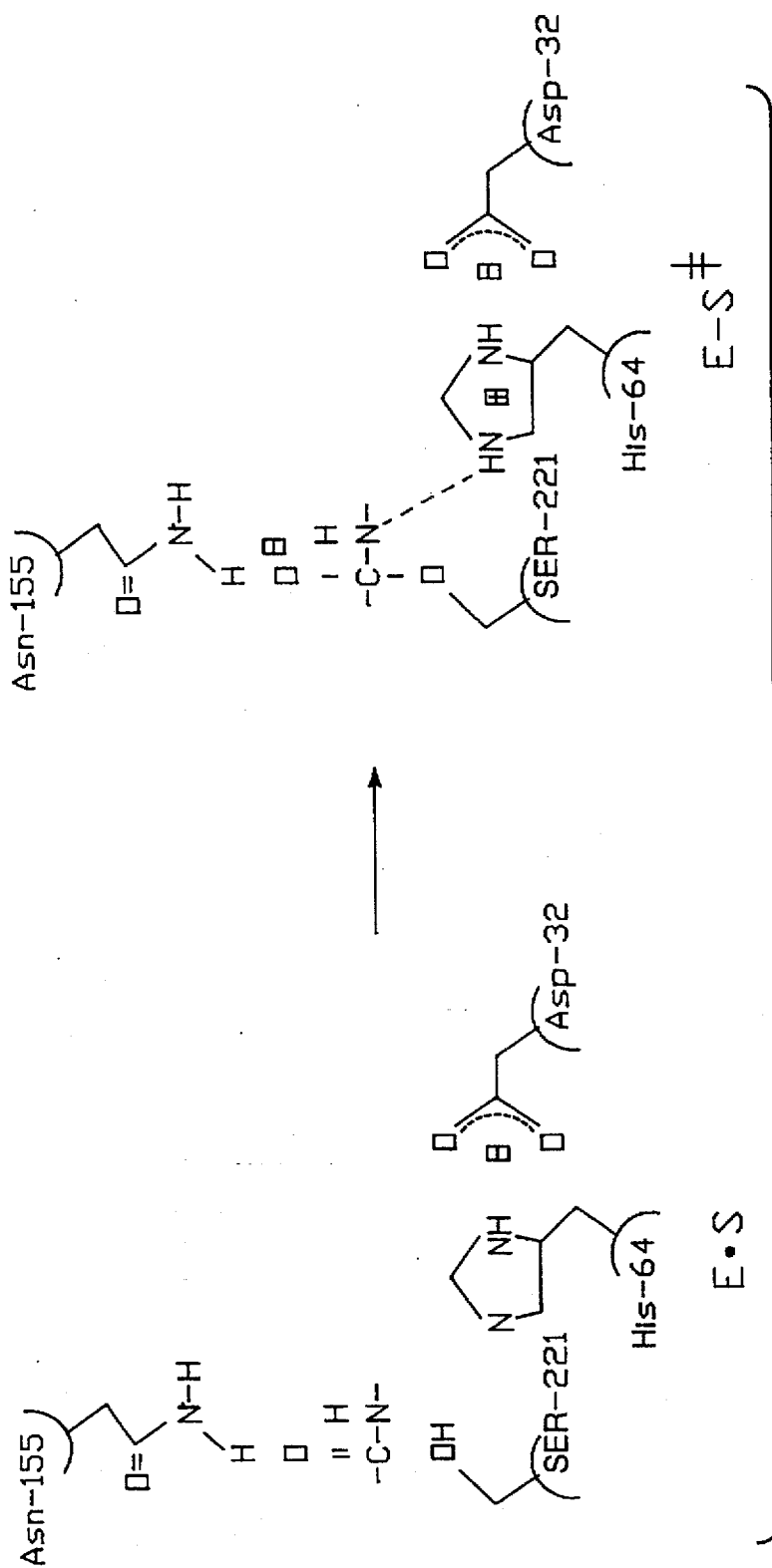
FIG._3

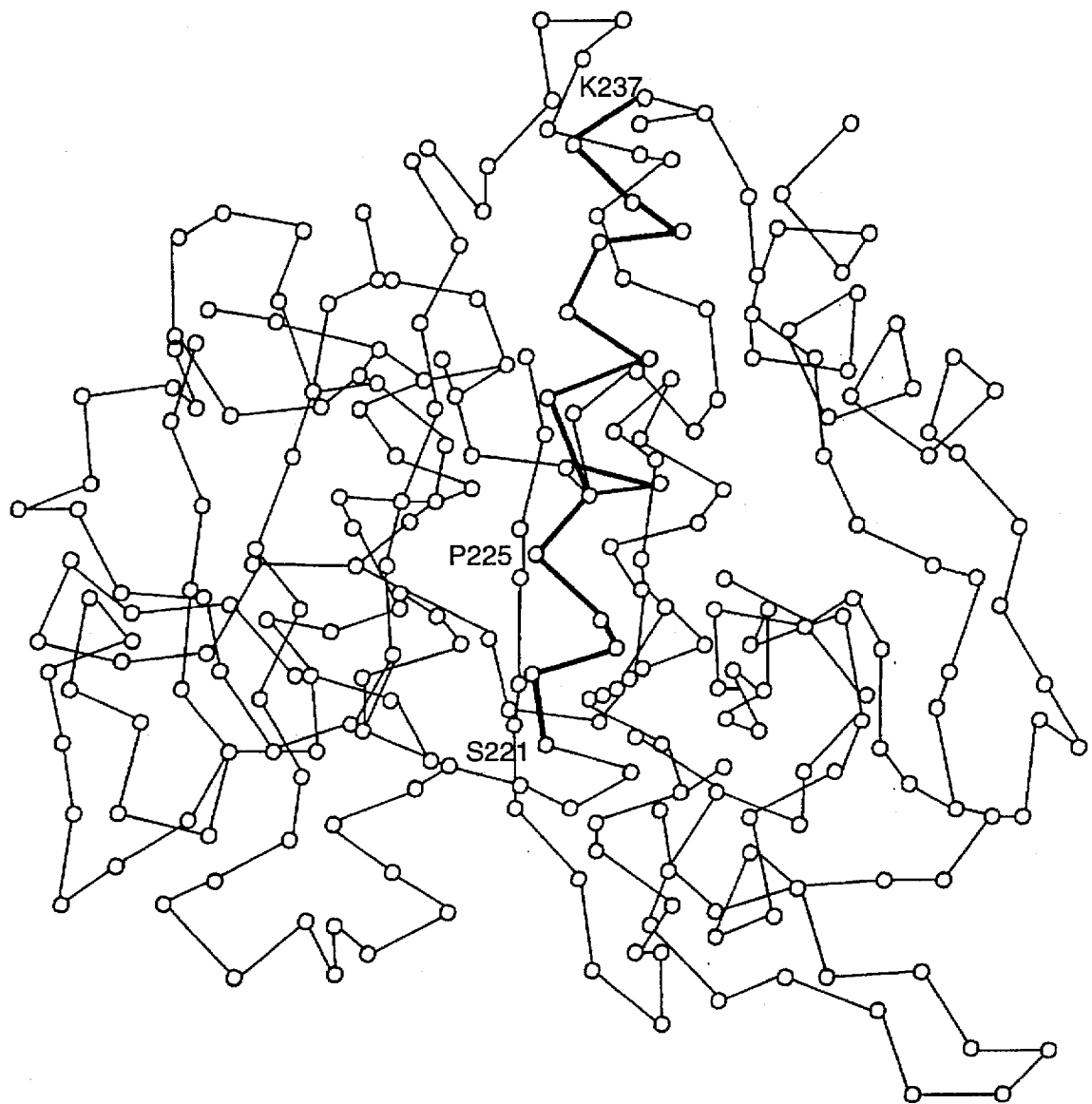
FIG._4

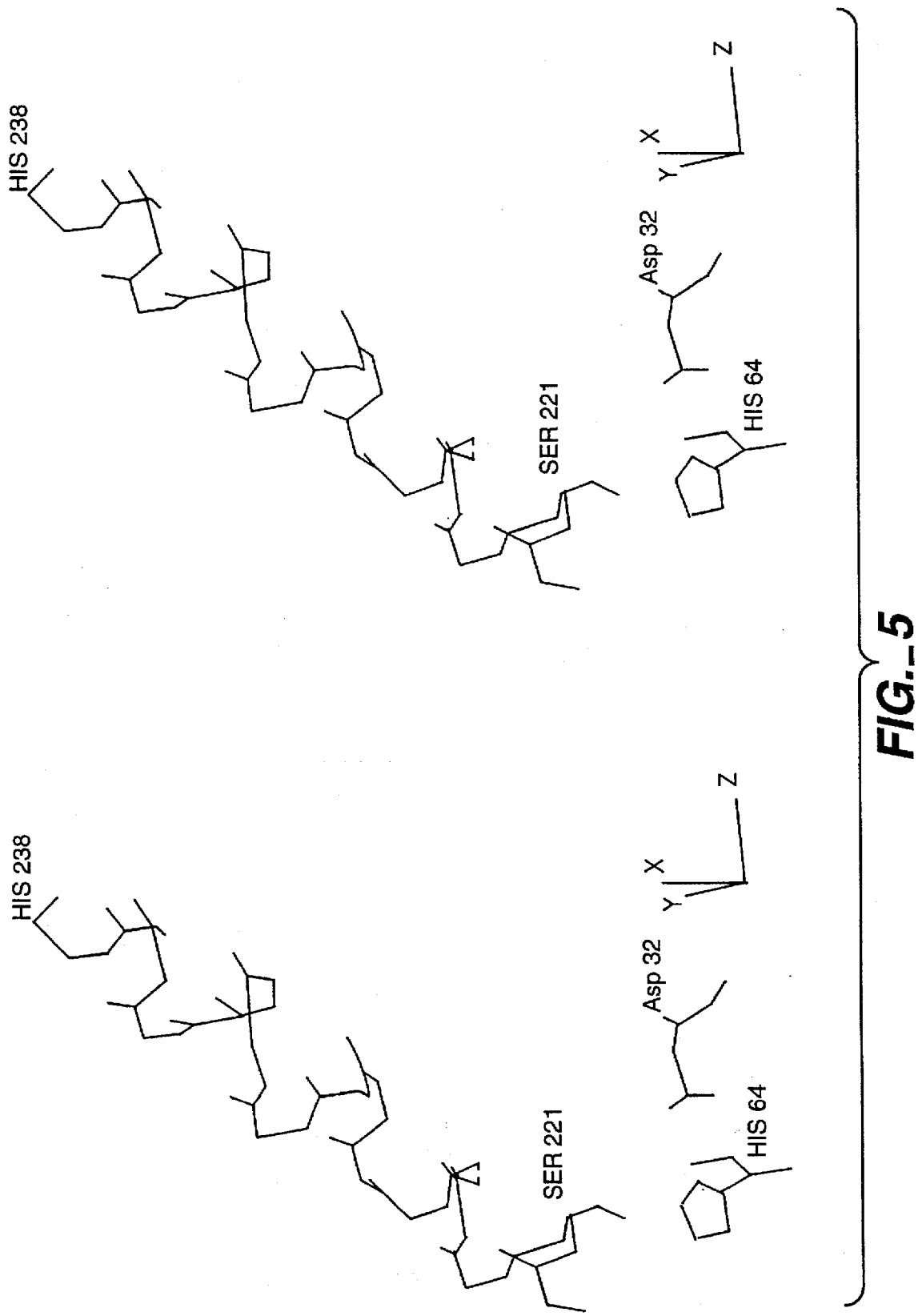
FIG._5

HOMOLOGY of BACILLUS PROTEASES
1. Bacillus Amyloliquefaciens
2. Bacillus Subtilis var. I168
3. Bacillus Licheniformis (Carlsbergensis)

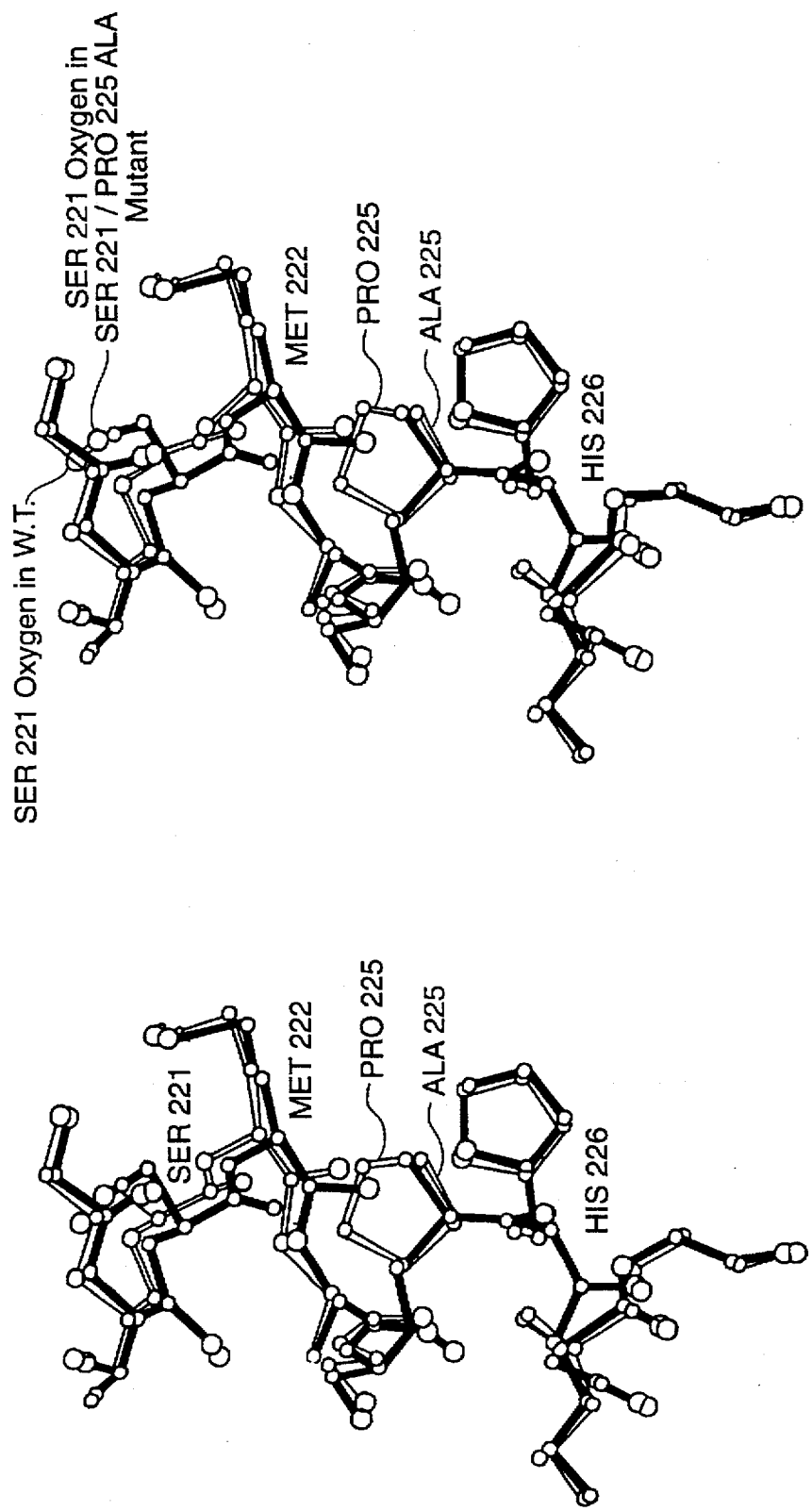
FIG._7

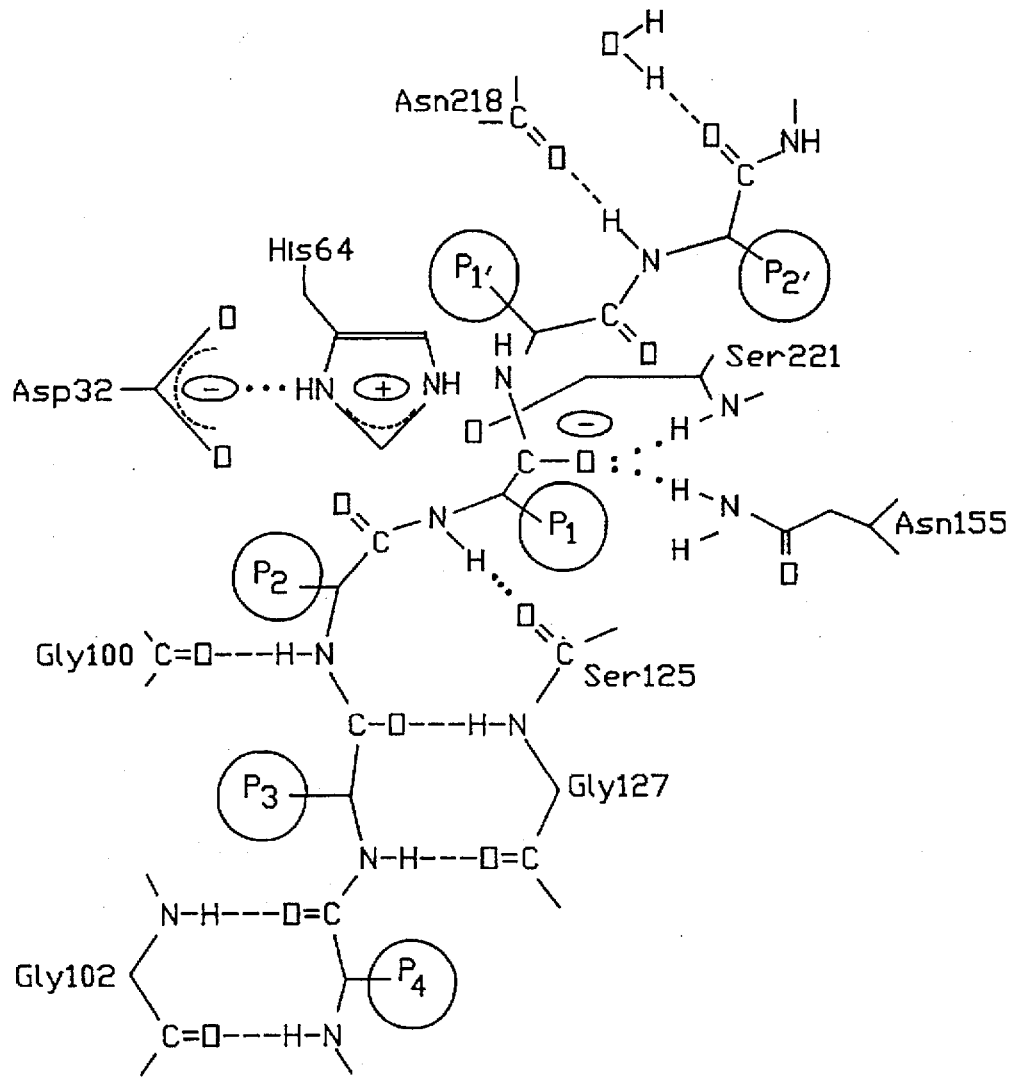
FIG._8
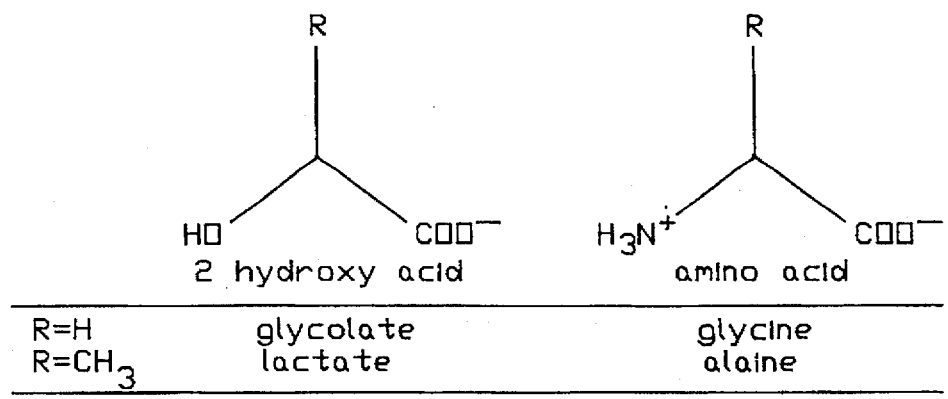
FIG._9

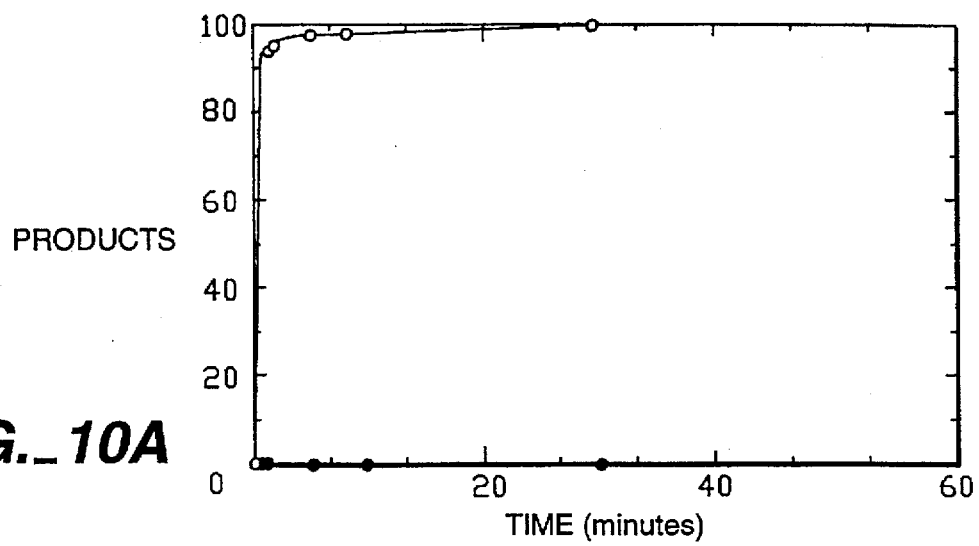
FIG._10A
FIG._10B
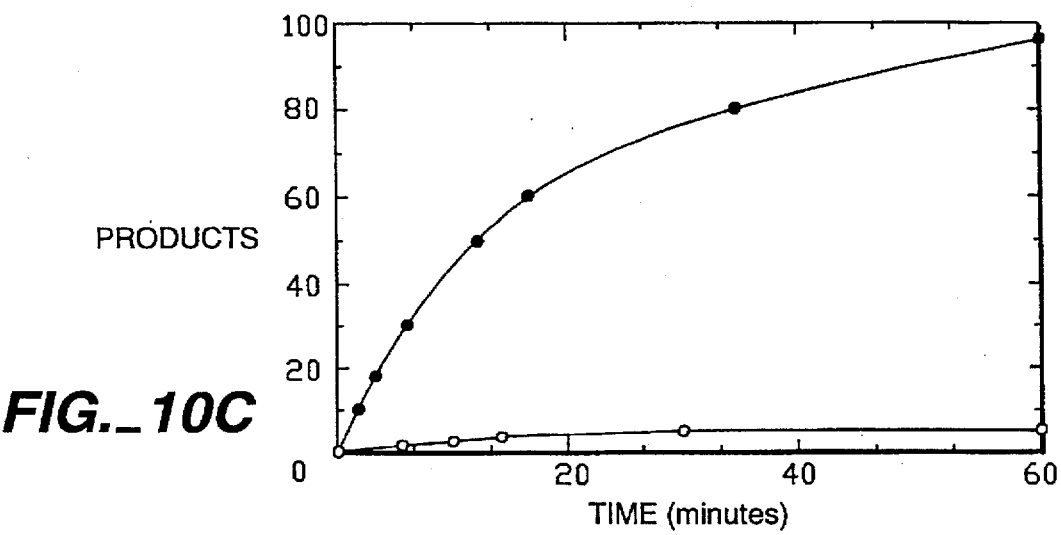
FIG._10C

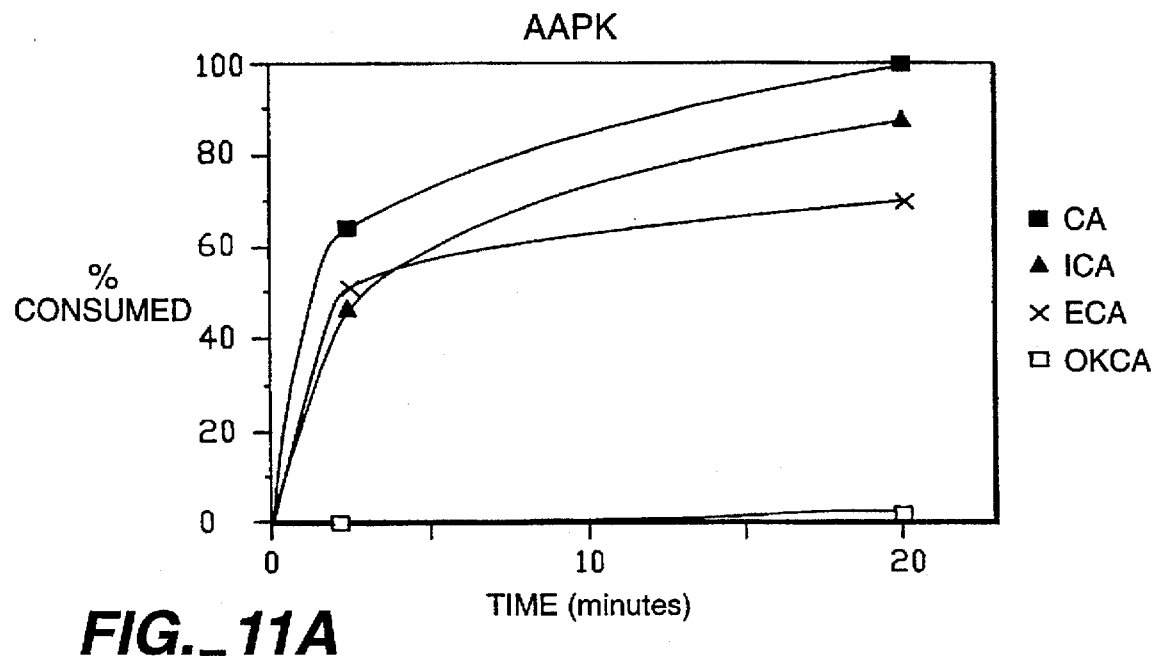
FIG._11A
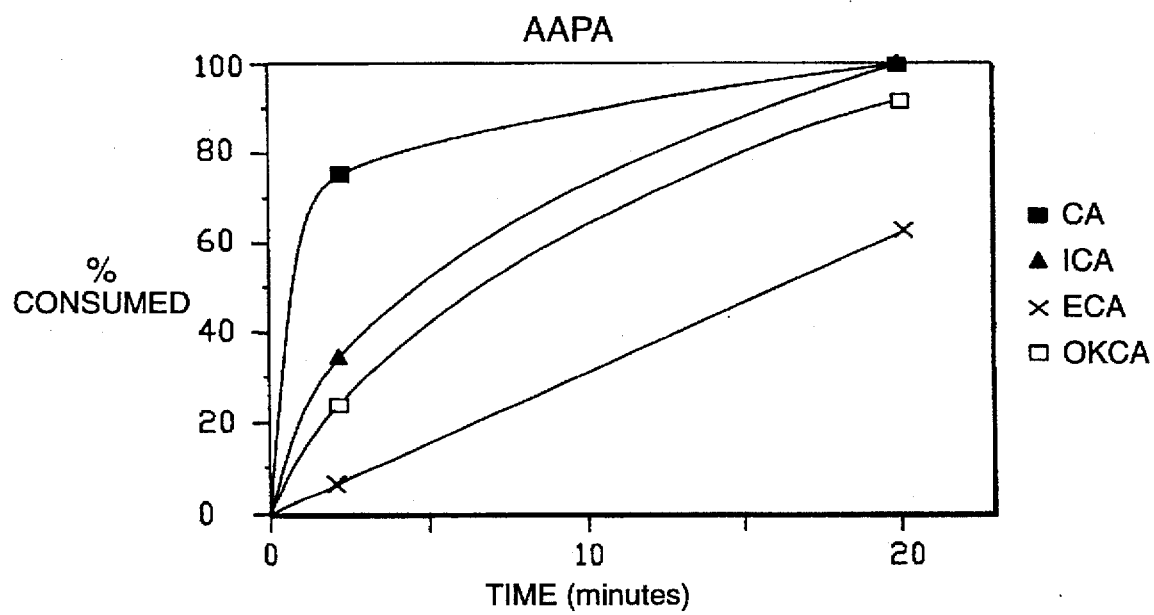
FIG._11B

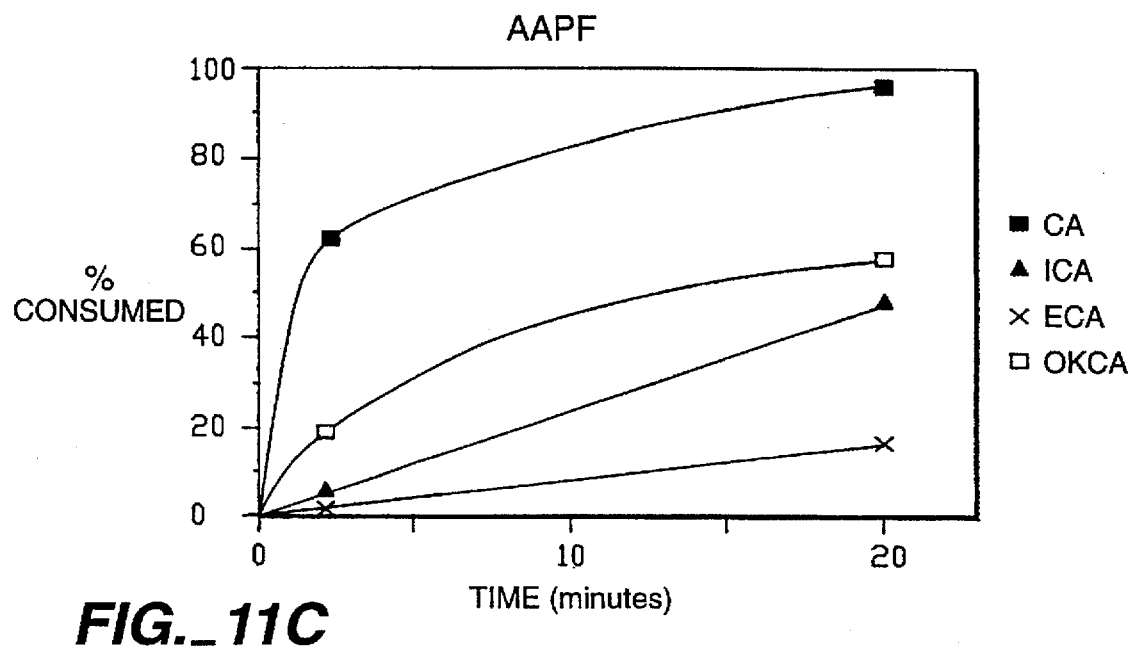
FIG._11C
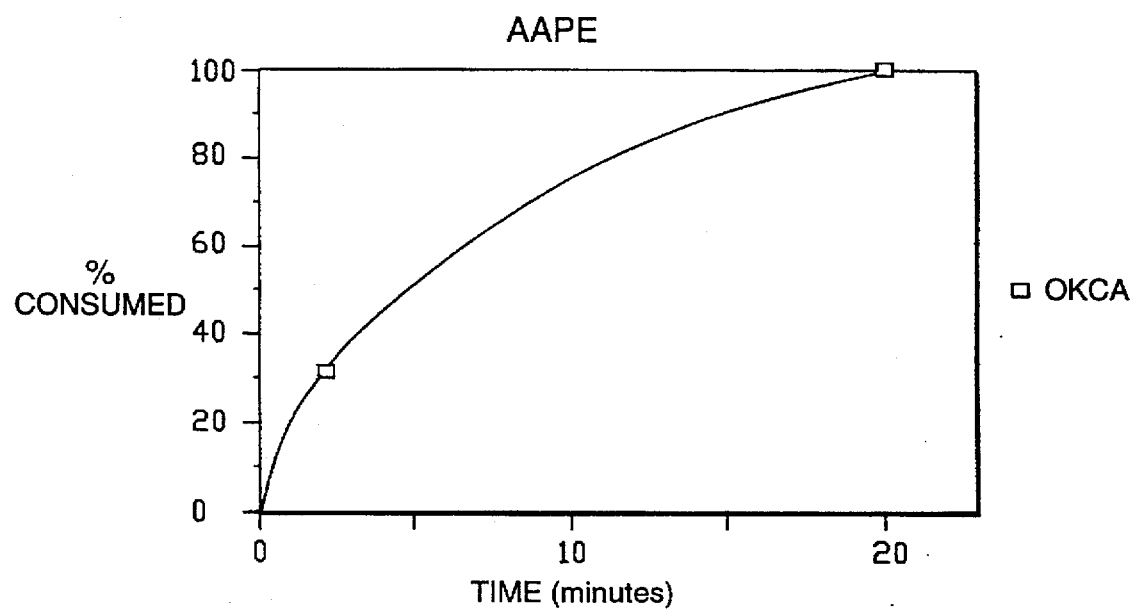
FIG._11D

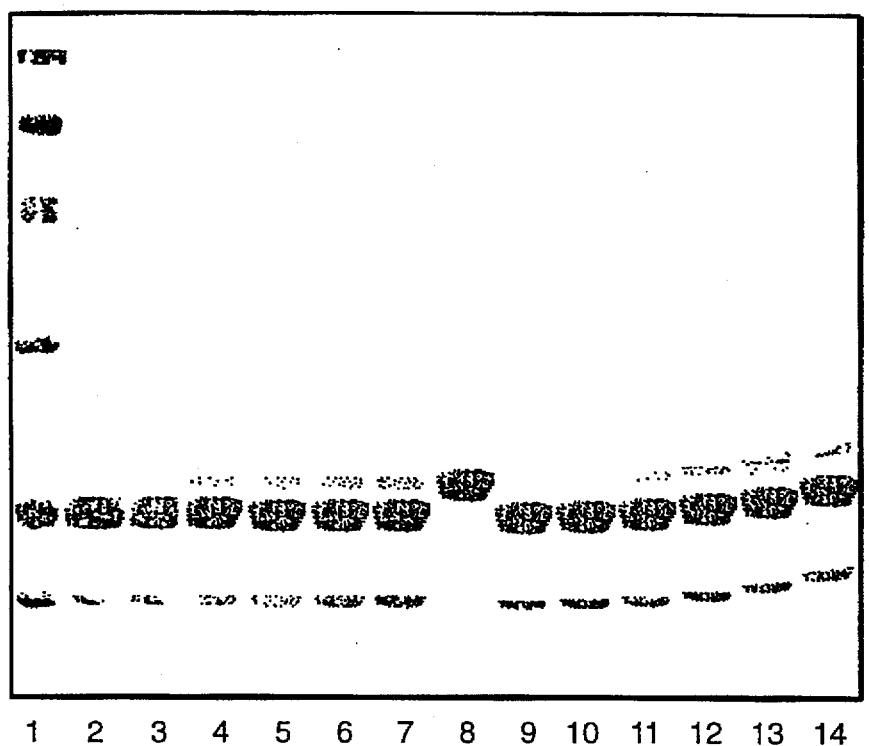
FIG._12
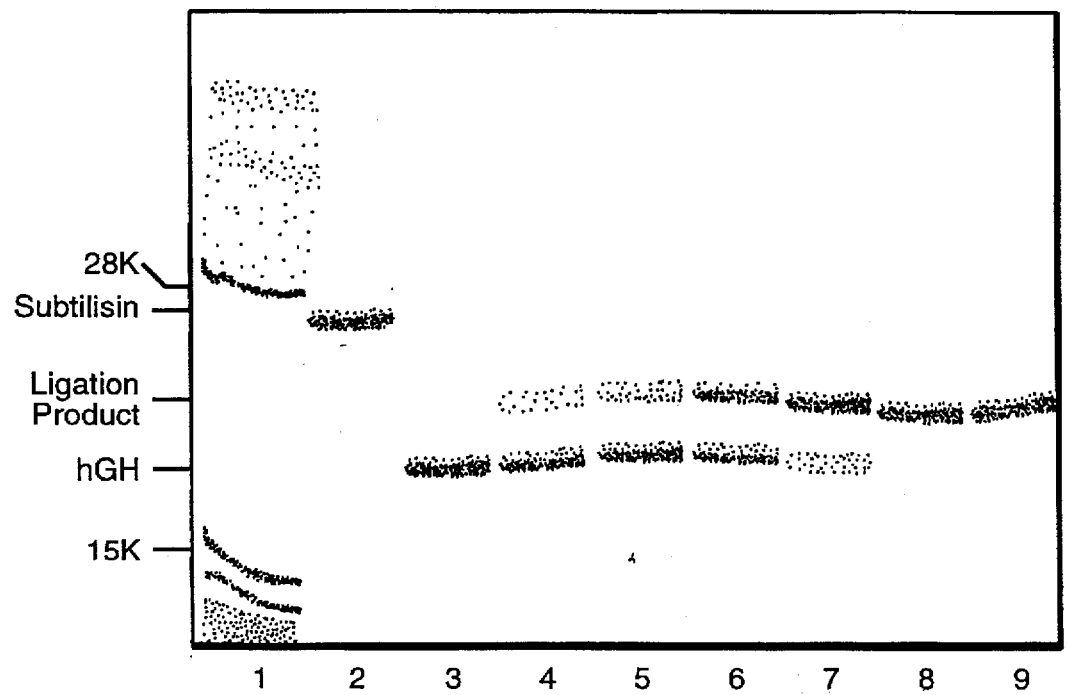
FIG._14

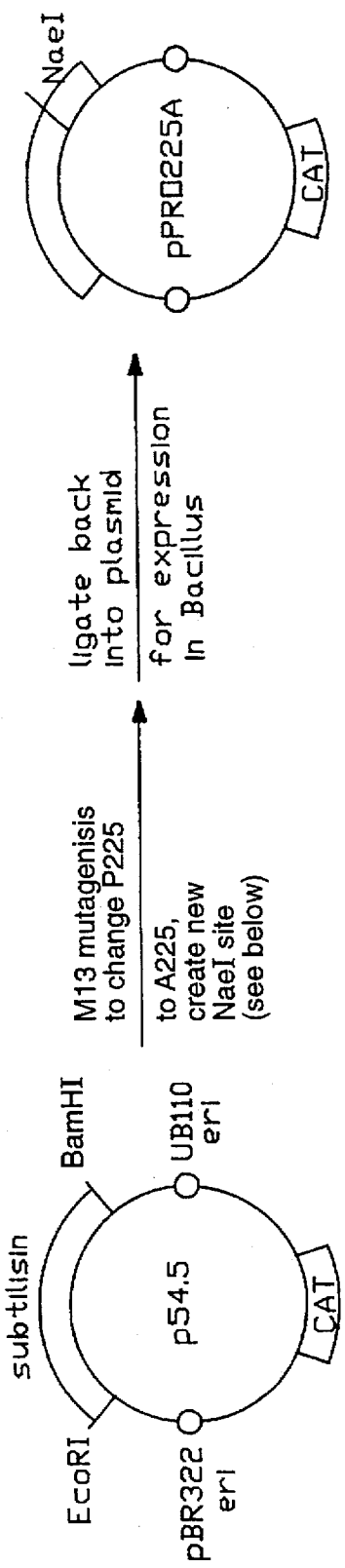
FIG._13

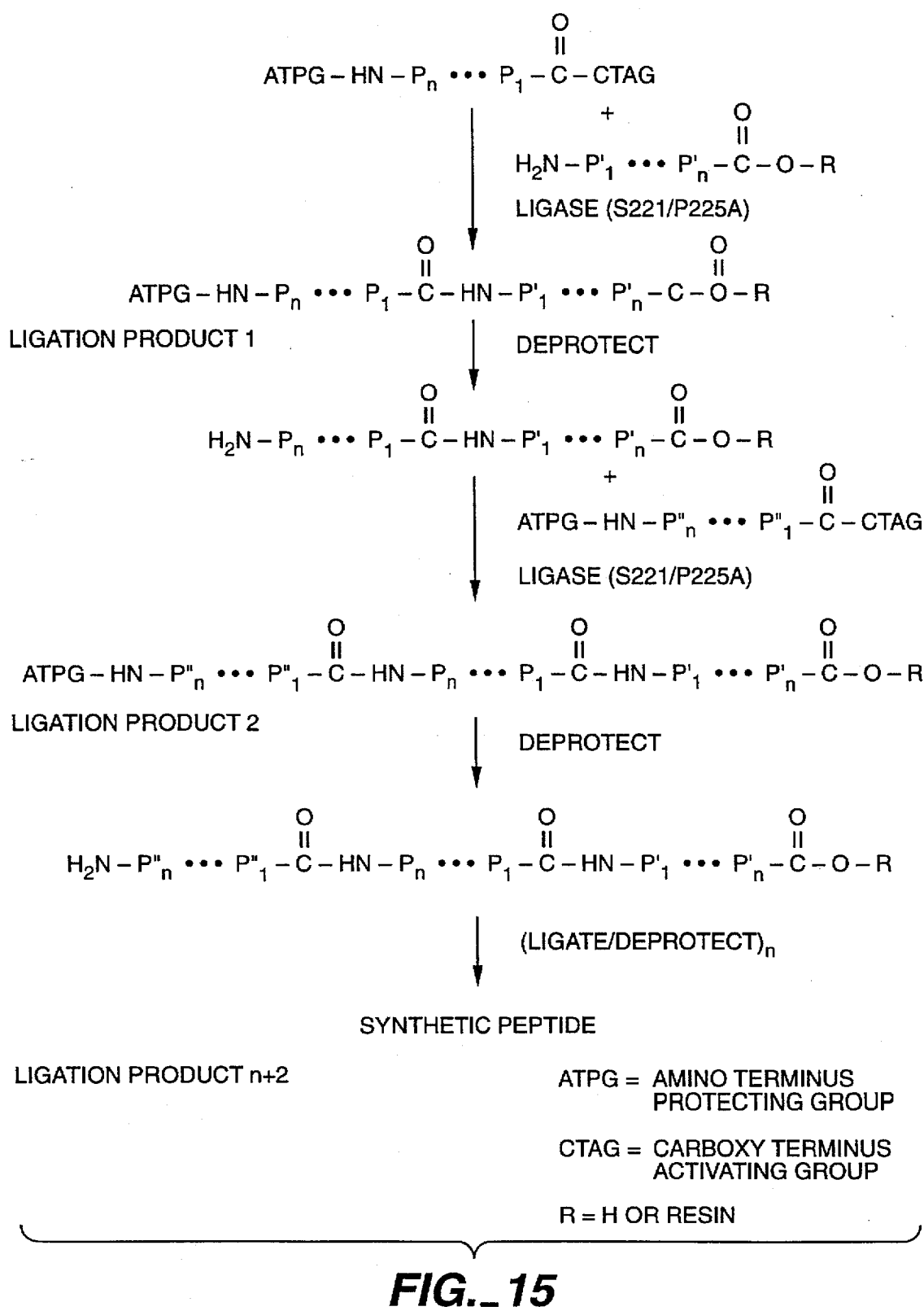
FIG._15 iNocHN-STMSITDCRETGSSKYPNCAY-CO$_2$R + H$_2$N-KTTQANKHIIVACEGNPYVPVHFDASV-CO$_2$

↓ LIGASE iNocNH-STMSITDCRETGSSKYPNCAYKTTQANKHIIVACEGNPYVPVHFDASV-CO$_2$

↓ Zn/CH$_3$CO$_2$H

H$_2$N-STMSITDCRETGSSKYPNCAYKTTQANKHIIVACEGNPYVPVHFDASV-CO$_2$

↓ 1) iNocHN-ACKNGQTNCYQSY-CO$_2$R/Ligase  2) Zn/CH$_3$CO$_2$H

↓ 1) iNocHN-ADVQAVCSQKNV-CO$_2$R/Ligase  2) Zn/CH$_3$CO$_2$H

↓ 1) iNocHN-SSSNYCNQMMKSRNLTKDRCKPVNTFVHESL-CO$_2$R
   2) Zn/CH$_3$CO$_2$H

↓ 1) SucHN-KETAAAKFERQHMDSSTSAA-CO$_2$R/Ligase

SucHN-KETAAAKFERQHMDSSTSAASSSNYCNQMMKSRNLTKDRCKPVNTFVHESLADVQAVCSQKNVAC
KNGQTNCYQSYSTMSITDCRETGSSKYPNCAYKTTQANKHIIVACEGNPYVPVHFDASV-CO$_2$H

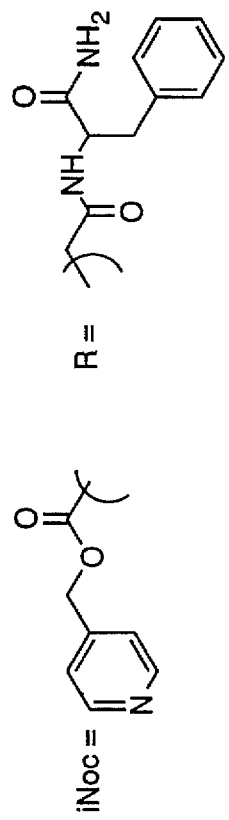

*FIG._16*

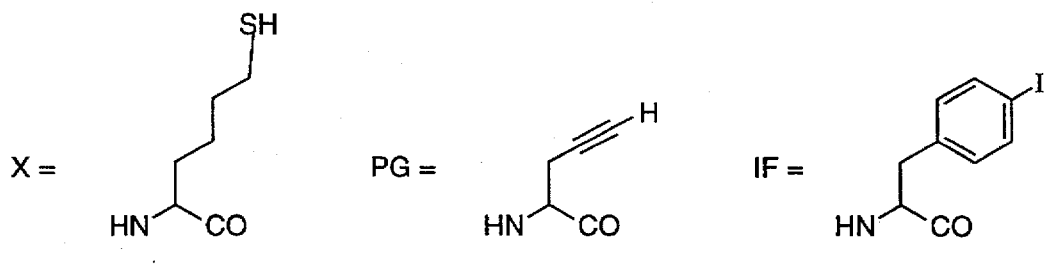
FIG._17

SERINE PROTEASE VARIANTS HAVING PEPTIDE LIGASE ACTIVITY

This Application is a divisional of Ser. No. 08/386,000, filed 09 Feb. 1995, now U.S. Pat. No. 5,629,173, which is a divisional of Ser. No. 08/218,873, filed 28 Mar. 1994, now abandoned which is a continuation of Ser. No. 08/013,445, filed 04 Feb. 1993, now abandoned, which is a continuation-in-part of PCT/U.S. Ser. No. 91/05480, filed 06 Aug. 1991, which is a continuation-in-part of Ser. No. 07/566,026, filed 09 Aug. 1990, abandoned.

TECHNICAL FIELD OF THE INVENTION

The invention relates to serine protease variants derived from precursor serine proteases via recombinant and/or chemical methods to form protease variants having improved peptide ligase activity. The invention also includes novel ligation substrates which in combination with the serine protease variants and a second ligation substrate are capable of forming a ligation product. The invention also relates to methods for forming such ligation products and the products formed thereby.

BACKGROUND OF THE INVENTION

Chemical approaches for synthesis and engineering of proteins offer many advantages to recombinant methods in that one can incorporate non-natural or selectively labelled amino acids. However, peptide synthesis is practically limited to small proteins (typically <50 residues) due to the accumulation of side-products and racemization that complicate product purification and decrease yields (for recent reviews see Kaiser, E. T. *Acc. Chem. Res.* 22: 47–54(1989); Offord, R. E. *Prot. Eng.* 1:151–157 (1987)).

Proteolytic enzymes, in particular serine proteases, have reportedly been used as alternatives to synthetic peptide chemistry because of their stereoselective properties and mild reaction conditions (for reviews see Kullman, W. (1987) In: Enzymatic Peptide Synthesis, CRC Press, Florida U.S.; Chaiken, *CRC Crit. Rev. Biochem.* 11: 255–301 (1981)). Such enzymes reportedly have been used to complement chemical coupling methods to produce larger peptides by blockwise enzymatic coupling of synthetic fragments. Inouye et al., *J. Am. Chem. Soc.*, 101: 751–752 (1979)(insulin fragments); Hommandberg and Laskowski, *Biochemistry* 18: 586–592 (1979) (ribonuclease fragments) ). However, the narrow substrate specificities and intrinsic hydrolytic (peptidase) activity of serine proteases have limited their use in peptide synthesis.

A central problem in the case of serine proteases in peptide synthesis is that hydrolysis of the acyl-enzyme intermediate is strongly favored over aminolysis (FIG. 1). Several laboratories have reported that the equilibrium is shifted from hydrolysis toward aminolysis by use of mixed or pure organic solvents to carry out catalysis (Coletti-Previero et al., *J. Mol. Biol.* 39: 493–501 (1969); Barbas et al., *J. Am. Chem. Soc.* 110: 5162–5166 (1988). However, enzymes are generally less stable and relatively insoluble in organic solvents (Wong et al., *J. Am. Chem. Soc.* 112, 945–953 (1990); Klibanov, (1986) *Chemtech* 16, 354–359). Further, kinetic activation barriers in organic solvents are higher for the charged transition-states involved leading to lower enzymatic activity. In an attempt to avoid these problems, one laboratory reported that thiolsubtilisin, a derivative of the bacterial serine protease in which the active site Ser221 was chemically converted to a Cys (S221C), shifted the preference for aminolysis to hydrolysis by >1000-fold for very small peptides. Nakasuta et al. (1987) *J. Am. Chem. Soc.* 109, 3808–3810. This shift was attributed to the kinetic preference of thioesters to react with amines over water. Based upon similar principles, another laboratory reported that selenolsubtilisin had a 14,000-fold shift in preference for aminolysis over hydrolysis. Wu and Hilvert (1989) *J. Am. Chem. Soc.* 111, 4513–4514. However the catalytic efficiencies for aminolysis of a chemically activated ester by either thiol- or selenolsubtilisin are about $10^3$- and $10^4$-fold, respectively, below the esterase activity of wild-type subtilisin. Although chemically active esters have reportedly been used to increase the rates for acylation of thiol- or selenolsubtilisin (e.g. the acylation of thiolsubtilisin with a p-chlorophenyl ester of an 8-mer peptide for ligation with a 4-mer peptide in >50% DMF), such activated esters present synthetic difficulties as well as creating substrates prone to spontaneous hydrolysis in aqueous solvents (Nakatsuka et al. (1987) supra.).

The serine proteases comprise a diverse class of enzymes having a wide range of specificities and biological functions. Stroud, R. M. (1974) *Sci Amer.* 131, 74–88. Despite their functional diversity, the catalytic machinery of serine proteases has been approached by at least two genetically distinct families of enzymes: the Bacillus subtilisin-type serine proteases and the mammalian and homologous bacterial trypsin-type serine proteases (e.g., trypsin and *S. gresius* trypsin). These two families of serine proteases show remarkably similar mechanisms of catalysis. Kraut, J. (1977) *Ann. Rev. Biochem.* 46, 331–358. Furthermore, although the primary structure is unrelated, the tertiary structure of these two enzyme families bring together a conserved catalytic triad of amino acids consisting of serine, histidine and aspartate.

Subtilisin is a serine endoprotease (MW~27,500) which is secreted in large amounts from a wide variety of Bacillus species. The protein sequence of subtilisin has been determined from at least four different species of Bacillus. Markland, F. S., et al. (1971) in *The Enzymes,* ed. Boyer, P. D., Acad. Press, New York, Vol. III, pp. 561–608; Nedkov, P. et al. (1983) *Hoppe-Seyler's Z. Physiol. Chem.,* 364, 1537–1540. The three-dimensional crystallographic structure of subtilisin BPN' (from *B. amyloliquefaciens*) to 2.5 Å resolution has also been reported. Bott, et al. (1988), *J. Biol. Chem.,* 263, 7895–7906; McPhalen, et al. (1988), *Biochemistry.* 27, 6582–6598; Wright, C. S., et al. (1969), *Nature,* 221, 235–242; Drenth, J. et al. (1972) *Eur. J. Biochem.,* 26, 177–181. These studies indicate that although subtilisin is genetically unrelated to the mammalian serine proteases, it has a similar active site structure. The x-ray crystal structures of subtilisin containing covalently bound peptide inhibitors (Robertus, J. D., et al. (1972), *Biochemistry,* 11, 2439–2449), product complexes (Robertus, J. D., et al. (1972) *Biochemistry* 11, 4293–4303), and transition state analogs (Matthews, D. A., et al (1975) *J. Biol. Chem.* 250, 7120–7126; Poulos, T. L., et al. (1976) *J. Biol. Chem.* 251, 1097–1103), which have been reported have also provided information regarding the active site and putative substrate binding cleft of subtilisin. In addition, a large number of kinetic and chemical modification studies have been reported for subtilisin (Philipp, M., et al. (1983) *Mol. Cell. Biochem.* 51, 5–32; Svendsen, I. B. (1976) *Carlsberg Res. Comm.* 41, 237–291; Markland, F. S. Id.). Stauffer, D. C., et al. (1965) *J. Biol. Chem.* 244, 5333–5338; Polgar, L. et al. (1981) Biochem. Biophys. Acta 667, 351–354).

U.S. Pat. No. 4,760,025 discloses subtilisin mutants wherein a different amino acid is substituted for the naturally-occurring amino acid residues of *Bacillus amy-*

*loliquifaciens* subtilisin at positions +32, +155, +104, +222, +166, +64, +33, +169, +189, +217, or +156.

The references discussed above are provided solely for their disclosure prior to the filing date of the present case, and nothing herein is to be construed as an admission that the inventors are not entitled to antedate such disclosure by virtue of prior invention or priority based on earlier filed applications.

SUMMARY OF THE INVENTION

Based on the foregoing, it is apparent that the chemical synthesis of large peptides and proteins is severely limited by the available chemical synthesis techniques and the lack of an efficient peptide ligase which is capable of coupling block synthetic or recombinant peptides.

Accordingly, it is an object herein to provide serine protease variants which are capable of efficiently ligating peptides and other substrates.

Further, it is an object herein to provide ligation substrates which when used in combination with the aforementioned serine protease variants are capable of ligating a first ligation substrate with a second ligation substrate to form a ligation product.

Further, it is an object herein to provide methods for producing ligation products using serine protease variants and ligation substrates.

Further, it is an object herein to provide ligation products made by the aforementioned methods.

In accordance with the foregoing objects, the invention includes serine protease variants having an amino acid sequence not found in nature which are derived from a precursor serine protease by at least two changes in the amino acid residues of the precursor serine protease. In particular, the precursor serine proteases are characterized by a catalytic serine residue which participates in the catalysis normally carried out by the precursor enzyme. This active site serine residue is replaced with a different amino acid to substitute the nucleophilic oxygen of the serine side chain with a different nucleophile. Alternatively, the side chain of the active site serine may be directly modified chemically to substitute a different nucleophile for the nucleophilic oxygen. The second change comprises replacement or modification of a second amino acid residue not consisting of the active site serine of the precursor enzyme. Such replacement or modification of the second amino acid residue, in combination with the replacement or modification of the active site serine, produces a serine protease variant characterized by a peptide ligase activity measured in aqueous solution which is greater than that of a different serine protease variant containing only the substitution or modification of the nucleophilic oxygen at the active site serine.

The invention also includes ligation substrates which are useful in combination with the aforementioned serine protease variants. In various precursor serine proteases, the enzyme catalyzes the cleavage of a peptide bond (the scissile peptide bond). The standard designation of protease hydrolysis substrate residues using the nomenclature of Schechter and Berger, *Biochem. Biophys. Res. Commun.* 27: 157–162 (1967) and the scissile bond hydrolyzed is shown in FIG. 2A. Since peptide ligation is essentially the reversal of hydrolysis, ligation substrates are defined similarly as depicted in FIG. 2B. Thus, in one aspect of the invention, first ligation substrates comprise at least an R1 amino acid residue with the carboxy terminus of the R1 residue esterfied with an organic alcohol (e.g. a 2-hydroxy carboxylic acid) or thiol. The R1 residue comprises those amino acid residues R1 which preferentially bind to the precursor serine hydrolase or which preferentially bind to those serine hydrolase variants which have been further modified to alter substrate specificity at the P1 position. Such R1 residues also comprise non-naturally occurring amino acids for which the variant has specificity. In addition, the esterified 2-hydroxy carboxylic acid closely resembles the P1' residue in substrates for the precursor serine protease or the residues preferred by those serine protease variants whose specificity has been modified at the P1' position.

The invention also includes ligation methods wherein the serine protease variant of the invention is contacted with a first and a second ligation substrate to form a ligation product. The first ligation substrate comprises the aforementioned ligation substrate (FIG. 2B). The second ligation substrate comprises at least an R1' amino acid residue for which the serine protease variant has specificity (FIG. 2C). It may also comprise non-naturally occurring amino acids for which the variant has specificity. The ligation product so formed by a ligation of the first and second ligation substrate contains the sequence R1–R1' (FIG. 2D).

In addition, the invention includes ligation products made by the aforementioned method. Such products typically have a length greater than about 17 amino acid residues. Such ligation products are also characterized by the ligation method which may be carried out in, but not limited to, aqueous solution.

BRIEF DESCRIPTION OF THE DRAWINGS

FIG. 1 depicts the kinetic aspects of peptide ligation. In Equation 1, the ester bond is cleaved by the enzyme, the alcohol group leaves and the acid becomes acylated to the active site nucleophile to form an acyl-enzyme intermediate (acyl-enzyme). Two possible reactions of the acyl-intermediate are hydrolysis (Equation 2) and aminolysis (Equation 3). Hydrolysis is nonproductive whereas aminolysis leads to adduct formation. The amidase activity of the enzyme (Equation 4) results in cleavage of the adduct and reformation of the acyl-enzyme intermediate.

FIG. 2A depicts the protease substrate residues designated using the nomenclature of Schechter and Berger (1967) *Biochem. Biophys. Res. Commun.*, 27 157–162. FIGS. 2B and 2C depict first and second ligation substrates used in peptide ligation. The various residues R2, R1, R1' and R2' comprise amino acid residues or analogues to such residues for which the serine protease variant or precursor enzyme has specificity, e.g. those amino acid residues comprising P2, P1, P1' and P2'. The carboxy terminus of the first ligation substrate contains Group X which is a 2-hydroxy carboxylic acid esterified to the C-terminal carboxyl group of the substrate used to form the first ligation substrate. The residues R2", etc. comprise amino acid residues or analogous to such residues for which the protease variant or precursor enzyme has specificity, e.g. P2', etc. FIG. 2D depicts the ligation product formed by ligation of the first and second ligation substrates (FIGS. 2B and 2C) by the serine protease variants of the invention.

FIG. 3 depicts the catalytic residues of *Bacillus amyloliquefaciens* subtilisin including the catalytic triad Ser221, His64 and Asp32. The tetrahedral intermediate transition state is shown as ES$^+$.

FIG. 4 depicts the tertiary structure of subtilisin from *Bacillus amyloliquefaciens* subtilisin. The α-helix of subtilisin associated with the catalytic residue Ser221 is highlighted.

FIG. 5 is a stereo view of the α-helix of *Bacillus amyloliquefaciens* subtilisin associated with the catalytic Ser221.

FIG. 6 depicts the amino acid sequence for subtilisin from *Bacillus amyloliquefaciens*, *Bacillus subtilis* VarI168 and *Bacillus licheniformis* using standard single letter designations for naturally occurring amino acids.

FIG. 7 is a stereo view overlay of wild-type (open bar) and P225A (solid bar) *Bacillus amyloliquefaciens* subtilisin in the region containing α-helix containing Ser221 and position 225.

FIG. 8 depicts an active site view showing a peptide substrate in the transition state bound to the active site of wild-type subtilisin (residues P4 through P2'). The hydrolysis substrate is bound in an outstretched β-sheet like conformation with the main chain carbonyl oxygens and amides involved in hydrogen bonds with corresponding groups of the enzyme. Specifically, the residues S1–S4 form the central strand of a three-stranded antiparallel β-sheet (McPhalen et al., (1988) supra.). Some of the more important side chain interactions on either side of the scissile bond are emphasized. Other residues affecting substrate specificity, e.g. Glu156 and Gly166 for P1 specificity, are not shown.

FIG. 9 depicts the general structure and specific 2-hydroxy carboxylic acids that are useful in making first ligation substrates that mimic a peptide substrate. The structural relationship between specific 2-hydroxy and amino acids is also depicted.

FIGS. 10A, 10B and 10C depict progress curves showing the consumption of peptide ester substrate (succinyl-Ala-Ala-Pro-Phe-glycolate-Phe-amide at a starting concentration of 0.35 mM) and the concurrent appearance of hydrolysis and aminolysis products using the dipeptide Ala-Phe-amide (3.6 mM) as the nucleophile (acyl-acceptor) with different subtilisin variants. The same amount of enzyme (10 μM) was used in each case under identical conditions, pH 8.0, (25°±0.2° C.). Aliquots were taken a various times and analyzed by RP-HPLC. The subtilisin variant was Pro225Ala in FIG. 10A, Ser221Cys in FIG. 10B, and Ser221Cys/Pro225Ala in FIG. 10C (Aminolysis (●), Hydrolysis (○)).

FIG. 11 is a comparison of subtilisin variants having different P-1 specificities with each of four alternative first ligation substrates. Progress curves show the consumption of substrate turning into hydrolysis- and aminolysis products in the presence of 1.5 mM of the nucleophile ligation peptide Ala-Phe-amide. The substrates are abbreviated to their tetra peptide in the one-letter form, i.e., AAPF is s-Ala-Ala-Pro-Phe-glycolate-Phe-amide. In each case, aminolysis predominates over hydrolysis.

FIG. 12 shows reducing SDS-PAGE of time course aliquots of growth hormone ligations using either a first ligation substrate ester of the natural first eight amino acids or a first ligation peptide modified to become more suited for the wild type specificity of subtilisin. The second ligation substrate was des-octa hGH. Lane 1, Low molecular weight standard; Lanes 2 and 9, non-ligated des-octa hGH; Lanes 3–7, aliquots from the reaction using the G166E/S221C/P225A version of the peptide ligase with the peptide ester of the natural N-terminus, after times 1, 10, 20, 40 and 80 minutes; Lane 8, wild type growth hormone; Lane 10–14, aliquots from the reactions using the S221C/P225A form of the ligase with the alternative peptide ester, after times 1, 10, 20, 40 and 80 minutes. In all lanes containing the des-octa mutant hGH, two smaller bands can be seen below the major band. These are the two chains resulting from a proteolytic cut during the expression and purification from *E. coli*. Furthermore, in all time points aliquots of the subtilisin variant may be seen at an apparent weight of about 30 kDa.

FIG. 13 depicts the method of construction of DNA encoding the replacement of proline at position 225 *Bacillus amyloliquefaciens* subtilisin with alanine.

FIG. 14 shows reducing SDS-PAGE of time course aliquots of Protropin ligations. A nine residue peptide was ligated onto Protropin using the Ser221Cys/Pro225Ala version of the peptide ligase. Lane 1, low molecular weight standard; Lane 2, subtilisin; Lane 3, unligated Protropin; Lanes 4–9, hGH ligated with a peptide after 1,2,5,10,30 and 60 minutes.

FIG. 15 depicts a representative flow diagram and synthetic strategy employing the ligase (S221C/P225A) for synthesis of a large synthetic peptide. The substrates of the ligase may be synthetic (e.g. solid or liquid phase), isolated (naturally occurring or recombinant) or combinations thereof. The amino terminus protecting groups (ATPG's) prevent improper ligation and are deprotected under conditions different from any sidechain deprotection. Deprotection of ligation products between each ligation step. Carboxy terminus activating groups (CTAG's) facilitate acylation of the ligase prior to aminolysis.

FIG. 16 Flow diagram for synthesis of Wild-type Ribonuclease A. ATPG is iNOC and CTAG(R) is glc-F-amide. Deprotection of iNOC is carried out with Zn and acetic acid.

FIG. 17 Incorporation of unnatural amino acids into Ribonuclease A.

DETAILED DESCRIPTION

As used herein, "serine protease" refers to a protease which contains at least one catalytically active serine residue. Such serine proteases are ubiquitous being found in both procaryotic and eucaryotic organisms. A common characteristic of many serine proteases, such as the subtilisin-type and trypsin-type serine protease, is the presence of a common catalytic triad comprising aspartate, histidine and serine. In the Subtilisin-type proteases, the relative order of these amino acids, reading from the amino to carboxy terminus is aspartate-histidine-serine. In the trypsin-type proteases, the relative order, however, is histidine-aspartate-serine. Notwithstanding this relative sequence orientation of the catalytic residues, the secondary and tertiary structure of serine proteases bring these three catalytic residues into close proximity to form the catalytically active site.

FIGS. 3 and 5 depict the catalytic residues of *Bacillus amyloliquefaciens* subtilisin. The interactions of serine 221 in subtilisin to form a tetrahedral transition state with the carbon of the scissile peptide bond is shown in FIG. 3. An acyl-enzyme intermediate between the catalytic serine and the carboxy portion of the substrate is formed after the carboxy terminal portion of the substrate leaves the active site. Hydrolysis of the acyl-enzyme intermediate releases the amino terminal portion of the cleaved peptide from the enzyme and restores the serine alcohol group.

In subtilisin-type serine proteases, the OG group of the catalytic side chain of serine (serine-221 in subtilisin) is located near the amino terminus of a long central α-helix which extends through the molecule. Bott, et al. (1988) *J. Biol. Chem.* 263, 7895–7906. In *Bacillus amyloliquefaciens* subtilisin this α-helix comprises methionine 222 through lysine 237. This helix is conserved in evolutionarily related subtilisin-type serine proteases but is not found in the catalytic sites of trypsin-type serine proteases. McPhalen, et al. (1988) *Biochemistry* 27, 6582–6598. The α-helix associated with the active site of subtilisin-type serine proteases has led to the suggestion that the dipole of this helix may have a functional role in catalysis. Hol, W. G. J. (1985) *Prog. Biophys. Molec. Biol.* 45, 149–195. The lack of α-helix at the active site of the trypsin-type serine proteases, however, has raised the unresolved question of whether the active site helix of subtilisin-type serine proteases is of any significance in catalysis. Hol (1985) supra.

In FIG. 4, the α-helix of *Bacillus amyloliquefacien* subtilisin together with the catalytic serine 221 is shown as it relates to the tertiary structure of the enzyme. A stereo view of this α-helix associated with the catalytic serine 221 is shown in FIG. 5.

The amino acid sequence for subtilisin from *Bacillus amyloliquefaciens*, *Bacillus subtilis* VarI168 and *Bacillus licheniformis* is shown in FIG. 6. The α-helix in *Bacillus amyloliquefaciens* subtilisin extends from Met222 Lys237. The corresponding (equivalent) α-helix in *Bacillus subtilis* is the same and in *Bacillus lichenformis* subtilisin comprises Met221 to Lys236. The corresponding (equivalent) residue of Proline 225 in *Bacillus amyloliquefaciens* subtilisin is also Proline 225 in *Bacillus subtilis* and Proline 224 in *Bacillus licheniformis* subtilisin.

The catalytic serine in *Bacillus subtilis* is at position 221 and at position 220 in *Bacillus lichenformis* subtilisin.

As used herein, a "precursor serine protease" refers to a naturally occurring serine protease and recombinant serine proteases. Examples of naturally occurring precursor serine proteases include the bacterial subtilisins from *Bacillus amyloliquefaciens*, *Bacillus licheniformis*, *Bacillus amylosaccaridicus*, and homologous serine protease from fungi, plant and higher animal species, trypsin-type serine proteases from bacteria fungi, plant, animal and virus including trypsin, chymotrypsin, α-lytic protease, elastase, plasminogen, thrombin, tissue plasminogen activators and homologs thereof.

"Recombinant serine proteases" refers to serine proteases in which the DNA sequence encoding the naturally occurring serine proteases modified to produce a variant DNA sequence which encodes the substitution, insertion or deletion of one or more amino acids in the serine protease amino acid sequence. Suitable modification methods are disclosed herein and in EPO Publication No. 0 130 756 published Jan. 9, 1985 and EPO Publication No. 0 251 446 published Jan. 7, 1988. When a particular serine protease is referred to, e.g. subtilisin, the term precursor subtilisin and recombinant subtilisin are used consistent with these definitions.

In addition to naturally occurring and recombinant serine proteases, the term "precursor serine protease" also includes "synthetic serine proteases" which are naturally occurring or recombinant serine proteases which contain one or more amino acid residues which are not naturally occurring. Such synthetic serine proteases may be made by the methods described herein or by in vitro transcription-translation methods as disclosed by Schultz, et al., *Science.* 244: 182–188 (1989).

As used herein a "serine protease variant" refers to a serine protease having an amino acid sequence which is derived from the amino acid sequence of a precursor serine protease. The amino acid sequence of the serine hydrolase variant is "derived" from the precursor protease amino acid sequence by the substitution, deletion or insertion of one or more amino acids of the precursor amino acid sequence. Such modification is of the "precursor DNA sequence" which encodes the amino acid sequence of the precursor serine protease. Further, in some instances, the serine protease variant may be derived from the precursor protease by the direct chemical modification of one or more side chains of the amino acid residues of the precursor amino acid sequence. For example, in one of the preferred embodiments the serine 221 of *Bacillus amyloliquefaciens* subtilisin is converted to cysteine. Such conversion may be obtained by modifying the DNA sequence of subtilisin to encode cysteine thereby replacing serine with cysteine in the variant or by the direct modification of serine with an appropriate chemical agent to form the equivalent variant. See e.g. Neet, K. E., et al (1966), *Proc. Natl. Acad. Sci. USA,* 56, 1606–1611; Polgar, L., et al. (1966), *J. Amer. Chem. Soc.,* 88, 3153–3154, which describe the chemical modification of subtilisin to form thiolsubtilisin.

In the preferred embodiments, the nucleophilic oxygen of the side chain of an active site serine residue is replaced or modified to substitute the nucleophilic oxygen of that side chain with a different nucleophile. Preferred nucleophiles include —SH, —SeH, —NH$_2$. The most preferred nucleophile is SH— representing the replacement of serine with cysteine.

In addition, the serine protease variants of the invention include the replacement or modification of a second amino acid residue in the precursor serine protease. The modification of this second amino acid residue is made to perturb the active site to accommodate the changes induced therein by the substitution or modification of the side chain of the active site serine residue. When the active site serine has been replaced or modified to produce a side chain which is larger than the naturally occurring serine side chain (e.g. when cysteine replaces serine or selenium replaces the nucleophilic oxygen), the second amino acid residue is a residue which upon replacement or modification causes the new nucleophilic catalytic side chain to be displaced in a way which effectively increases the size of the active site. Thus, for example, in the case of the subtilisin-type serine proteases, the nucleophile residing at position 221 in *Bacillus amyloliquefaciens* subtilisin may be moved by modifying one or more amino acid residues in the a-helix which is located at or near the active site serine in the precursor serine protease. In the case of subtilisin, such modification or replacement is preferably of proline 225 (Caldwell, et al., *J. Cell. Biochem. Supp.,* 13A: 51(1989)). Modification of this residue in *Bacillus amyloliquefaciens* subtilisin, or an equivalent residue in other subtilisins, is by replacement with a helix-forming amino acid. Chou, P. Y., et al., *Biochemistry,* 13: 211 (1974); Kyte, J., et al., *J. Mol. Biol.,* 157: 105 (1982); Rose, G., et al., *J. Mol. Biol.,* 113: 153 (1977). Examples of such amino acids include alanine, leucine, methionine, glutamine, valine and serine. Helix breaking amino acids such as glycine and proline are not preferred. Alternatively, replacement amino acids comprise those which have a smaller side chain volume than the residue being replaced. Chothia *Ann. Rev. Biochem.,* 53: 537 (1984). Replacement with the aforementioned amino acids or their analogs modifies the discontinuity (kink) preceding residues 223–237 in the α-helix.

A preferred replacement amino acid for position 225 is alanine. When such a variant is made, the α-helix containing Ser221 is known to move the —OH nucleophile away from the oxyanion hole. The effect of this particular replacement on naturally occurring subtilisin is shown in FIG. 7 which is a stereo view of residues 220 through 230 of wild type and Pro225Ala subtilisin. The —OH nucleophile of Ser221 is moved away from the oxyanion hole and the catalytic histidine 64 by 0.2 to 0.4 Å. When combined with the replacement of Ser221 with cysteine, this displacement of the 221 residue effectively offsets the increase in nucleophile size of 0.65 Å and 1.03 Å, respectively. Pauling, L. (1960) in *The Nature of the Chemical Bond*, 3d ed., Cornell Univ. Press, Ithica, N.Y., pp. 246–260.

A characteristic of the serine protease variant of the invention is that it has peptide ligase activity in aqueous solution which is greater than that of a different serine protease containing only the substitution or modification of the nucleophilic oxygen of the active site serine residue. Thus, variants such as Ser221Cys/Pro225Ala have greater peptide ligase activity than the Ser221Cys variant.

As used herein, "peptide ligase activity" refers to the ability of an enzyme to ligate two or more substrates. Such substrates include the ligation substrates described hereinafter as well as known activated peptides such as peptide thiobenzyl esters p-chlorophenyl esters (Nakatsuka, et al. *J. Amer. Chem. Soc.*, 109: 3808–3810 (1987)), p-nitrophenyl esters and other aryl esters. In addition, activated esters include alkyl esters such as methyl, ethyl, glycolate, lactate, etc. and akylthiol esters. Peptide ligase activity is measured by contacting the enzyme of interest with at least two peptides or substrates (one of which generally contains an activated carboxy terminus) under conditions favorable for ligation. The kcat, Km and/or kcat/Km ratio is then determined for that enzyme. kcat refers to the turn-over number of the enzyme, and gives the maximal number of substrate molecules that can be converted to product per unit time per enzyme molecule. The Km is usually inversely proportional to the affinity of substrate(s) for the enzyme. The catalytic efficiency which is the second order rate constant for the conversion of substrate to product is given as the kcat/Km ratio. Variant serine proteases having higher kcat/Km ratios for the same peptide ligation have greater peptide ligase activity. However, they can also be considered to have greater peptide ligase activity if they have improved kcat assuming that the reactions can be run where the enzymes are saturated with substrates. When comparing the peptide ligase activity of two enzymes, each enzyme is preferably contacted with the same peptides under the same conditions.

In addition to the above described modifications of the active site serine and a second amino acid residue to form serine protease variants having ligase activity, various other replacement or modifications of amino acid side chains may be made to modify specificity for the ligation peptides used to form a desired ligation peptide product. For example, the subtilisin variant Ser221Cys/Pro225Ala is derived from the wild type subtilisin from *Bacillus amyloliquefaciens*. This wild type subtilisin preferentially hydrolyzes peptides wherein the P1 residue for the hydrolysis peptide shown in FIG. 2A consists of phenylalanine, tyrosine, tryptophan, leucine, methionine and lysine but not Thr, Val, Ile, Pro or Gly. In addition, preferred hydrolysis peptides should not contain Ile, Pro, Asp or Glu at the P1' position or small amino acids such as Gly, Ala, Pro, Ser, Asp or Thr at the P2' position. In the subtilisin variant Ser221Cys/Pro225Ala, the amino acid residues forming the substrate binding cleft of subtilisin are not modified and accordingly the various enzyme subsites within this binding cleft which interact with one or more of the substrate residues, e.g. P2 through P2', are still capable of binding the normal substrate for the wild type subtilisin. Of course, this variant demonstrates substantially reduced catalytic activity with such peptide substrate because of the modifications made to form the subtilisin variant.

Such a subtilisin variant, accordingly, is capable of binding ligation substrates containing amino acid residues or analogs corresponding to or closely related to those found in the normal peptide substrate. Thus, the "first ligation substrate" as schematically represented in FIG. 2B contains residues Rn through R1 (reading from the amino to carboxy terminus) wherein R1 is a large hydrophobic amino acid or analog similar to that normally found in the P1 position of a subtilisin hydrolysis substrate. Similarly, R2 corresponds to or is closely related to the amino acid residue (or its analog) normally found in position P2 of the hydrolysis substrate. The group X which is covalently linked to the carboxy terminus of the first ligation substrate and which activates the first ligation peptide and the residues R2" through Rn will be discussed in more detail hereinafter.

The "second ligation substrate" represented schematically in FIG. 2C contains residues R1' through Rn' (reading from the amino to carboxy terminus). When used with the above identified subtilisin variant modified at residues 221 and 225, R1' corresponds to the P1' amino acid residue (or its analog) in the normal subtilisin hydrolysis substrate. With regard to second ligation substrate residue R2', this residue comprises a large hydrophobic amino acid residue (or its analog) which is similar to or corresponds closely to the P2' residue of the normal subtilisin hydrolysis substrate. For both the first and second ligation substrates, other amino acid residues may be chosen to correspond to or be closely related to the amino acid residues (or their analogs) found in normal hydrolysis substrate. Appropriate R and R' residues for other serine protease are chosen but not limited to the natural hydrolysis substrates for such proteases.

In addition, either the first or second ligation substrate may include other compounds that result in the site specific modification of the product. The specific compounds may be chosen to specifically target certain sites within the product. For example, the first or second ligation substrate may contain heavy metal ions, that will result in heavy metal derivatives of the ligation product, useful in the X-ray crystallographic elucidation of the ligation product structure. The first or second ligation substrate may also contain modified or isotopically labelled amino acids for biophysical studies.

Furthermore, the conditions under which the ligation reactions are carried out may be modified as needed to allow ligation to occur. These modifications may be required to allow the ligation substrates to take the correct structural conformation for ligation to occur, without substantially destroying the ligase activity. For example, the experimental conditions may include the addition of denaturing reagents, detergents, organic solvents or reducing agents, or alterations in pH or temperature, amoung others.

The first and second ligation substrates, as well as the experimental conditions, may be selected as needed to produce the desired level of specificity. Some applications of the present invention may require lower levels of ligation reaction specificity, while in other applications strict specificities may be desirable.

As indicated herein, the subtilisin variant Ser221Cys/Pro225Ala is capable of ligating a first ligation substrate (containing an activation group) and a second ligation substrate in accordance with the above described preference for R1 and R2' amino acid residues. The peptide ligation activity for this variant is substantially greater than that of the Ser221Cys variant for the same ligation substrates. This variant's preference for first and second ligation substrates having amino acids Phe, Tyr, Met, Leu, Trp and Lys at position R1 and amino acids Phe, Tyr, Leu and Met at positions R2' provides substantial utility for ligating block substrates such as those made with known chemical synthetic techniques.

Synthetic ligation substrates are generally about 10–30 and preferably 15–25 residues long and typically produce a first ligation product having a length of about 50 residues. Such first ligation product may thereafter be ligated with another ligation substrate to build larger ligation products. This process is set forth in greater detail below.

In order to provide broader specificity for substrate ligation, other modifications may be made to the serine protease variant to change specificity for the first and/or second ligation substrate. As described herein, subtilisin variants containing the Ser221Cys/Pro225Ala modifications as well as modifications in the Glu156 and Gly166 residues were made to modify the specificity of the variant for the R1 residue of the first ligation substrate. Three variants of the Ser221Cys/Pro225Ala variant were made. These specific variants included the modifications 221 and 225 and further included Gly166Glu, Glu156Gln/Gly166Lys and Gly166Ile. Using the standard one-letter symbols for amino acid residues, these variants can be identified as G166E/S221C/P225A, E156Q/G166K/S221C/P225A and G166I/S221C/P225A respectively. By introducing these mutations into the S221C/P225A variant, the peptide ligase specificity was substantially altered. See FIG. 11 wherein the ligation of various first ligation substrates (discussed in more detail hereinafter) and the second ligation substrate Ala-Phe-amide is shown.

For a small R1 ester substrate (s-Ala-Ala-Pro-Ala-glc-Phe-amide) the G166I/S221C/P225A variant (ICA) is substantially better than the others (FIG. 11). The E156Q/G166K/S221C/P225A variant (QKCA) efficiently aminolyses a Glu R1 first ligation substrate with a second ligation substrate Ala-Phe-amide (AF-amide). It also has greater peptide ligation activity than the other variants toward a Phe R1 first ligation substrate. For a Lys R1 ester substrate the rates for three of the variants (including the complementary charged G166E/S221C/P225A variant (ECA)) are comparable and much more active than for the like charged mutant, E156Q/G166K/S221C/P225A. For ligation of peptide substrates containing an R1 Arg ester, our preliminary data indicates G165E/S221C/P225A is substantially more active than the parent ligase. See Table I.

In general, the aminolysis rates for the optimal enzyme ligation peptide pair were comparable indicating it should be possible to efficiently ligate Lys, Ala, Phe, and Glu R1 ligation substrates with the proper choice of S221C/P225A based ligase S221C/P225A (CA). Except for the Lys R1 ligation substrate, at least one of the three other specificity variants were significantly better than the parent peptide ligase. These additional variant enzymes should provide added flexibility in design of ligation junctions.

These results are consistent with the demonstrated specificity of subtilisin variants G166E, E156Q/G166K and G166I for hydrolysis of peptides containing Lys or Arg, Glu and Ala P1 substrates, respectively (Wells, et al. (1987)*Proc. Natl. Acad. Sci. USA*, 84, 1219–1223; Estell, et al. (1986), *Science*, 233, 659–663, and EPO Publication 0 251 446). It is expected that other modifications which are known to cause a change and/or shift in substrate specificity for various P and P' residues in wild type subtilisin can be effectively combined with the Ser221/Pro225 or equivalent modifications to further modify the specificity of the serine hydrolase variant for various first and second ligation substrates.

TABLE I

Summary of preferred sequences for ligating peptides using variants of subtilisin.

| | Residue | | | | | | |
|---|---|---|---|---|---|---|---|
| | P4 | P3 | P2 | P1 | R1' | R2' | R3' |
| Avoid: | | | | G,P,T,V,I | I,P,D,E[a] | P,G | |
| Preferred: | Small or large hydrophobics | flexible | flexible | M,Y,L(1)[b] F(1,4) K(1,2,3) R(3) A(2) E(4) | R,C,N T,K,H W,Q,Y A,V,S,G | F,Y L,M R,K | flexible |

[a] The deleterious effects of the Glu and Asp side-chains can be minimized in high salt (>1 M; Carter, et al., (1989), Proteins, 6, 240–248).
[b] These residues are preferred with the following variants of thiolsubtilisin: (1) = S221C/P225A; (2) = G166I/S221C/P225A; (3) = G166E/S221C/P225A; (4) = E156Q/G166K/S221C/P225A.

Many of these modifications to *Bacillus amyloliquefaciens* subtilisin are disclosed in EPO Publication 0 130 756 published Jan. 9, 1988, and EPO Publication No. 0 251 446, published Jan. 7, 1988. Such modifications may be readily made to the Ser221/Pro225 variants described herein (as well as other variants within the scope of the invention) to form variants having a wide range of specificity for first and second ligation substrates. The methods disclosed in these EPO publications may be readily adapted to modify the DNA encoding the variants described herein.

In addition to combining modifications which affect substrate substrate specificity, it is also possible to combine other modifications which affect other properties of the serine protease. In particular, modifications have been made to subtilisin which affect a variety of properties which may be desirable to combine with the variants of the present invention. For example, substitution of methionine at position 50 Phe or Cys and at position 222 with Ala, Gly, Ser and Cys results in a subtilisin variant which is oxidatively stable as compared to wild type subtilisin. In addition, there are known modifications to subtilisin which result in increased thermal stability, alkaline stability and changes in pH activity profile. See e.g. EPO Publication 0 251 446 published Jan. 7, 1988. The invention contemplates combining these and other possible modifications to form variants which in addition to having ligation activity are also characterized by changes in one or more other properties of the precursor enzyme. For example, serine protease variants which resist inactivation at higher temperatures than that of the variant not containing such modifications are useful to ligate first and second ligation substrates wherein an increase in reaction temperature facilitates a partial or complete denaturation of one or more of the ligation peptides to increase the ligation yield. Similarly, variants which have optimal activity at a pH which also facilitates denaturation of ligation substrate may prove useful in specific applications. Of course, various other modifications not presently known but which are found to confer desirable properties upon the serine protease variants of the invention are contemplated to be within the scope of the invention.

Although activated aryl-ester substrates (such as thiobenzyl esters) are more efficient than corresponding alkyl-esters to acylate subtilisin, aryl-esters are more difficult to synthesize and inherently less stable. A series of alkyl-ester substrates was prepared to improve upon their catalytic efficiencies as donor substrates for acyl-enzyme intermediate formation. Peptide substrates bind to subtilisin in an extended anti-parallel β-sheet conformation from residues P4 to P3' (McPhalen and James *Biochemistry*, 27: 6592–6598 (1988)). Although the P4 and P1 residues dominate the substrate specificity of the enzyme (for review see Philipp and Bender, *Mol. Cell. Biochem.*, 51: 5–32 (1983); Estell et al., *Science*, 233: 659–663(1986)), the catalytic efficiency for hydrolysis is enhanced significantly when peptide substrates are extended from P1' to P3' (Morahara et al., *Arch. Biochem. Biophys.*, 138: 515–525(1970)).

Referring to FIGS. 2B and 2C, first and second ligation substrates are shown with R1 and R2' groups being as previously described. The leaving group X in the ester in FIG. 2B may be any of the following organic alcohols or thiols: $C_6$–$C_{12}$ aryl where the aryl group is unsubstituted or substituted by one or more of the groups nitro, hydroxy, halo (F, Cl, Br, I), $C_1$–$C_8$ alkyl, halo-$C_1$–$C_8$ alkyl, $C_1$–$C_8$-alkoxy, amino, phenyloxy, phenyl, acetamido, benzamido, di-$C_1$–$C_8$ alkylamino, $C_1$–$C_8$ alkylamino, $C_6$–$C_{12}$ aroyl, $C_1$–$C_8$ alkanoyl, and hydroxy-$C_1$–$C_8$ alkyl, $C_1$–$C_{12}$ alkyl either substituted or unsubstituted, branched, straight chain or cyclo where the substituents are selected from halo (F, Cl, Br, I), $C_1$–$C_8$ alkoxy, $C_6$–$C_{12}$ aryloxy where the aryl group is unsubstituted or substituted by one or more of the groups nitro, hydroxy, halo (F, Cl, Br, I), $C_1$–$C_8$alkyl, $C_1$–$C_8$-alkoxy, amino, phenyloxy, acetamido, benzamido, di-$C_1$–$C_8$ alkylamino, $C_1$–$C_8$ alkylamino, $C_6$–$C_{12}$ aroyl, and $C_1$–$C_8$ alkanoyl, isothioureido, $C_3$–$C_7$ cycloalkyl, ureido, amino, $C_1$–$C_8$ alkylamino, di-$C_1$–$C_8$ alkylamino, hydroxy, amino-$C_2$–$C_8$ alkylthio, amino-$C_2$–$C_8$ alkoxy, acetamido, benzamido wherein the phenyl ring is unsubstituted or substituted by one or more of the groups nitro, hydroxy, halo (F, Cl, Br, I), $C_1$–$C_8$ alkyl, $C_1$–$C_8$-alkoxy, amino, phenyloxy, acetamido, benzamido, di-$C_1$–$C_8$ alkylamino, $C_1$–$C_8$ alkylamino, $C_6$–$C_{12}$ aroyl, $C_1$–$C_8$ alkanoyl, $C_6$–$C_{12}$ arylamino wherein the aryl group is unsubstituted or substituted by one or more of the groups nitro, hydroxy, halo, $C_1$–$C_8$ alkyl, $C_1$–$C_8$-alkoxy, amino, phenyloxy, acetamido, benzamido, di-$C_1$–$C_8$ alkylamino, $C_1$–$C_8$ alkylamino, $C_6$–$C_{12}$ aroyl, and $C_1$–$C_8$ alkanoyl, guanidino, phthalimido, mercapto, $C_1$–$C_8$ alkylthio, $C_6$–$C_{12}$ arylthio, carboxy, carboxamide, carbo-$C_1$–$C_8$ alkoxy, $C_6$–C aryl wherein the aryl group is unsubstituted or substituted by one or more of the groups nitro, hydroxy, halo, $C_1$–$C_8$ alkyl, $C_1$–$C_8$-alkoxy, amino, phenyloxy, acetamido, benzamido, di-$C_1$–$C_8$ alkylamino, $C_1$–$C_8$ alkylamino, hydroxy-$C_1$–$C_8$ alkyl, $C_6$–$C_{12}$ aroyl, and $C_1$–$C_8$ alkanoyl, and aromatic heterocycle wherein the heterocyclic groups have 5–10 ring atoms and contain up to two O, N, or S heteroatoms.

In one aspect of the invention, X is preferably a 2-hydroxy carboxylic acid. The general formula for a 2-hydroxy carboxylic acid is shown in FIG. 9. As can be seen therein, the core structure of the 2-hydroxy carboxylic acid is similar to the core structure for an amino acid except for the replacement of the amino group for the 2-hydroxy group. Accordingly, an appropriate side chain R group may be chosen for the 2-hydroxy acid to correspond to the side chain R groups found on naturally occurring amino acids. Thus, the various 2-hydroxy carboxylic acids e.g. glycolate corresponding to the amino acid glycine and lactate corresponding to the amino acid alanine, etc. may be esterified with the carboxy terminus of a substrate to form a first ligation substrate.

First ligation substrates were constructed wherein the 2-hydroxy carboxylic acid was glycolate or lactate. In essence, the 2-hydroxy carboxylic acid acts as an amino acid residue which may bind to that portion of the enzyme binding cleft which interacts with the P1' residue of a hydrolysis substrate. Further, the free-carboxyl group of the 2-hydroxy carboxylic acid may be amidated to form an amide or amidated with an amino acid residues (or analog) or peptide (or peptide analog) represented by R2" or R2" through Rn", respectively, as shown in FIG. 2B. As indicated therein, the R2" is preferably chosen to optimize the interaction with that portion of the binding cleft of the enzyme which normally interacts with the hydrolysis substrate residue P2'. Similar analogies exist for other R" residues. The leaving group thus obtained activates the first ligation substrate such that the activation energy for ester cleavage is lowered by optimizing binding to the serine protease variant.

As used herein, a "ligation product" is formed by ligation of first and second ligation substrate by the serine hydrolase variants of the invention. It is to be understood, however, that ligation products and the first and second ligation peptides need not be made entirely of naturally occuring amino acids and further need not be entirely proteinaceous. In this regard the only requirement of first and second ligation substrates is that they contain at least an R1 amino acid or functional analog thereof (at the carboxy terminus of the first ligation peptide) and an amino acid or functional analog at the R1' position of the second ligation peptide. Such R1 and R1' residues are capable of binding in the appropriate portion of the substrate binding cleft of the serine hydrolase variant such that ligation occurs. Specifically included in R1 and R1' are those amino acid residue analogs which are functional with the serine protease variants of the invention. Such analogs include L-selenocysteine, L-selenomethionine and L-propargylglycine (sigma).

To the extent that such binding and ligation also requires R2 and R2' amino acids (or their analogs) or additional amino acids R3 or R3', etc. (or their analogs) the first and second ligation substrates peptides will contain such structure. However, first and/or second ligation substrates may contain non-naturally occurring amino acids at postitions outside of the region required for binding and ligation. Further, since it is only necessary for the first and second ligation substrates to have sufficient binding to bring about ligation, the first and second ligation substrates and the corresponding ligation product formed therefrom may contain virtually any chemical structure outside of the necessary binding and ligation region. Accordingly, the invention is not limited to ligation substrates and ligation products which correspond to a polypeptide or protein containing naturally occurring amino acids.

The efficiency of peptide ligation using a series of glycolate and lactate-esters with S221C/P225A subtilisin was analyzed (Table II). As indicated, there is a systematic increase in kcat/KM of about 10-fold in extending esters from -glc-amide through -glc-Phe-Gly-amide. Most of this increase is the result of lower KM values. There is a similar progression starting from -lac-amide that further illustrates the advantage of extending the ester chain length. The lactate-ester series is generally 4- to 5-fold less reactive than the glycolate-ester series and contains an additional chiral center. Therefore, because of the improved catalytic efficiency and ease to synthesize, the -glc-Phe-amide ester substrate was further studied.

either of its parent single mutants for ligation of substrates using the -glc-Phe-amide-ester donor substrate.

TABLE III

Kinetic constants for the hydrolysis of an amide substrate (s-Ala—Ala—Pro—Phe—pNA) and for an activated ester substrate (s-Ala—Ala—Pro—Phe—Sbz). The ratio of esterase to amidase activities is the ratio of the apparent second order rate constants (kcat/KM). The aminolysis to hydrolysis ratio was investigated using the thiobenzyl ester substrate with 3.6 mM of the dipeptide Ala—Phe-amide as the nucleophile.

| enzyme | s-Ala—Ala—Pro—Phe—pNA | | | s-Ala—Ala—Pro—Phe—Sbz | | | esterase/ amidase | aminolysis/ hydrolase |
|---|---|---|---|---|---|---|---|---|
| | kcat | KM | kcat/MM | kcat | KM | kcat/MM | | |
| wild type[a] | $(4.4 \pm 0.01) \times 10^1$ | $(1.8 \pm 0.1) \times 10^{-4}$ | $(2.5 \pm 0.1) \times 10^5$ | $(2.3 \pm 0.1) \times 10^3$ | $(1.9 \pm 0.1) \times 10^{-4}$ | $(1.2 \pm 0.1) \times 10^7$ | $4.8 \times 10^1$ | $5.6 \times 10^{-3}$ |
| Pro225Ala | $4.1 \pm 0.04$ | $(7.8 \pm 0.2) \times 10^{-4}$ | $(5.2 \pm 0.1) \times 10^3$ | $(2.3 \pm 0.03) \times 10^3$ | $(3.8 \pm 0.1) \times 10^{-4}$ | $(6.2 \pm 0.1) \times 10^6$ | $1.2 \times 10^3$ | $1.6 \times 10^{-3}$ |
| Ser221Cys | $(1.3 \pm 0.04) \times 10^{-3}$ | $(4.9 \pm 0.4) \times 10^{-4}$ | $(2.7 \pm 0.1)$ | $1.4 \pm 0.1$ | $(5.5 \pm 0.3) \times 10^4$ | $9.3 \times 10^3$ | $3.0 \times 10^2$ | |
| 221Cys/ 225Ala | $<3 \times 10^{-5}$ | ND | ND | $(4.1 \pm 0.2) \times 10^1$ | $(1.9 \pm 0.2) \times 10^{-4}$ | $(2.1 \pm 0.2) \times 10^5$ | ND | $2.5 \times 10^1$ |

[a]Data for the pNA substrate and for the Sbz substrate from Carter and Wells (1988), Nature, 332, 564–568; and Wells, et al. (1986), Phil. Trans. R. Soc. Lond., A317 415–423, respectively.

TABLE II

Substrate leaving group comparison. The acyl-donor part is in all cases s-Ala-Ala-Pro-Phe- and is followed by the alternative leaving groups. The initial rate of ligation using the dipeptide -Ala-Phe-amide (3.1 mM) was measured. [a]The values of kcat/KM, the aminolysis fraction of the apparent second order rate constant for the reaction between the substrate and the enzyme, are the most reliable (error of about 20%).

| leaving group[a] | kcat (s$^{-1}$) | KM (mM) | $\frac{kcat(s^{-1}mM^{-1})^a}{KM}$ |
|---|---|---|---|
| -glc-amide | 9.5 | 3.0 | $3.20 \times 10^3$ |
| -glc-Phe-amide | 20.0 | 1.3 | $15 \times 10^3$ |
| -glc-Phe-Gly-amide | 20.0 | 0.6 | $34 \times 10^3$ |
| -lac-amide | 3.8 | 4.5 | $0.86 \times 10^3$ |
| -lac-Leu-amide | 2.3 | 1.9 | $1.2 \times 10^3$ |
| -lac-Phe-amide | 2.9 | 1.0 | $2.9 \times 10^3$ |
| -Sbz | 230.0 | 0.4 | $650 \times 10^3$ |

The P225A variant rapidly and quantitatively hydrolyzes the -glc-Phe-amide-ester with very little aminolysis (FIG. 10A). The S221C variant aminolyzes the substrate slowly and hydrolyzes the adduct (ligation product) so that during this time almost one-third of the substrate becomes hydrolyzed (FIG. 10B). However, the S221C/P225A variant gives rapid and almost quantitative aminolysis (>90%; FIG. 10C). Moreover, as expected from the very low amidase activity of S221C/P225A (Table III), the aminolysis product (ligation product) was not detectably hydrolyzed unlike the result using the S221C or P225A variants (data not shown). On the basis of rapid aminolysis and slow ligation product hydrolysis, S221C/P225A is a more useful enzyme than Sequence requirements for the nucleophilic acceptor peptide (second ligation substrate) were investigated by determining the ligation efficiency of a series of acceptor dipeptides having the form NH$_2$-R1'-Phe-amide, where R1' corresponds to the amino-terminal residue of the second ligation (acceptor) substrate that resides in the R1' binding site during attack of the thioacyl-enzyme intermediate. As the R1' residue is varied in side or charge (Gly, Ala, Leu, Arg) the apparent second order rate constant for aminolysis of s-Ala-Ala-Pro-Pro-Phe-glc-Phe-amide varies less than 7-fold (Table IV). This is consistent with the relatively broad specificity for hydrolyzing various P1' peptide substrates (Carter et al. (1989), Proteins. 6, 240–248).

TABLE IV

Comparison of efficiency in the aminolysis reaction of different di- and tri-amino acid peptides. The apparent second order rate constants for the reaction of the nucleophile with the peptide ligase acylated by s-Ala-Ala-Pro-Phe are compared.

| peptide[a] | peptide |
|---|---|
| GF 0.8 | GA 0.1 |
| AF 1.0 | GL 0.3 |
| LF 0.3 | FG 0.006 |
| RF 2.0 | AFA 2.0 |
| RG 0.04 | LFD 0.3 |

[a]The one-letter codes are used. All peptides were amidated at the carboxy terminus.

The R2' site was probed with a series of dipeptides having the form NH$_2$-Gly-R2'-amide (Table IV). Although there is a preference for larger hydrophobic amino acids, the rate constant for ligation varies only 8-fold in going from Ala to Leu to Phe for S221C/P225A. For some dipeptide combinations the difference can be much larger. For example, Arg-Phe is nearly 100-fold faster to aminolyze than Arg-Gly. Moreover, bad combinations, such as a large hydrophobic amino acid at R1' and Gly at R2' can make for extremely poor ligation substrates (compare NH$_2$-Phe-Gly-amide with NH$_2$-Gly-Phe-amide; Table IV). Extending the nucleophilic peptide can enhance the catalytic efficiency of ligation 2- to 3-fold (compare NH$_2$-Ala-Phe-amide with NH$_2$-Ala-Phe-Ala-amide; Table IV).

As a test for ligation of two large ligation substrates, a peptide ester was synthesized containing the first eight amino acids of hGH (FPTIPLSR) esterified to glycolate-Phe-amide (first ligation peptide). The acceptor peptide fragment was des-octa hGH, that contained residues 9–191 of hGH (second ligation peptide). The G166E/S221C/P225A variant produced ligation product after 80 min. having the expected molecular weight (FIG. 12). Amino-terminal sequencing of the first 10 residues of the product showed that a single FPTIPLSR fragment was ligated properly to the N-terminus of des-octa hGH beginning with sequence Leu-Phe-Asp to produce the full-length hormone. The parent peptide ligase (S221C/P225A) was significantly less efficient at ligating the two hGH peptide fragments. The improved efficiency of the G166E/S221C/P225A enzyme over the parent ligase is attributed to its increased activity for Arg R1 substrates due to the G166E substitution in the P1 binding site. Polymerization of the unprotected peptide ester was not observed. This is most likely the result of the Pro residue at the second amino acid residue of the first ligation peptide which is a very poor P2' residue (Carter and Wells, (1989), supra).

To demonstrate the utility of the ligase (S221C/P225A), a monomer ester first ligation substrate (FPTIPAAPF) was constructed that mimicked the optimal enzyme substrate (s-Ala-Ala-Pro-Phe-glc-Phe-amide). This peptide ester was ligated onto des octa hGH (second ligation substrate) by S221C/P225A (FIG. 12). Protein sequencing of the ligation product only gave the expected amino-terminal sequence, not the unreacted amino-terminus of des-octa hGH. This suggests that ligation only occurred to the α-amino-group of hGH and not to ε-amino-groups of lysine.

This semi-synthesis of hGH is the first example of ligation of peptide fragments in aqueous to form a large polypeptide. Previous ligation with thiolsubtilisin in solutions containing greater than 50% DMF (dimethylformamide) reportedly produced a peptide having a length of no longer than 17 amino acid residues. Nakatsuka, et al. (1987), *J. Am. Chem. Soc.*, 109, 3808–3810. In the ligation described herein, first and second ligation peptides were ligated with a serine protease variant of the invention to form a ligation product having 191 amino acid residues. Further, such ligation was accomplished in aqueous solution containing less than 2% by volume of nonaqueous solvent and did not require that peptide side-chains contain protector groups.

As used herein, the term "aqueous solution" refers to any solution that contains water. In some instances, an aqueous solution may comprise as little as 1% to approximately 5% water. However, an aqueous solution typically comprises greater than about 50% to 100% aqueous solution (excluding solutes). Accordingly, solutions containing a small percentage of nonaqueous solvent are considered to be within the scope of the definition of aqueous solution.

It is to be understood, however, that to the extent that the variants of the invention are only defined with regard to the peptide ligase activity of the serine protease variant in aqueous solution as compared to a variant modified only at the catalytic serine. This definition does not preclude use of the serine protease variants of the invention in solutions containing little or no water.

To demonstrate the utility of the protein ligase (S221C/P225A) in the total synthesis of a large polypeptide (i.e. longer than 50 amino acid residues ), wild-type Ribonuclease A was synthesized by the protein ligase method of this invention from totally synthetic ligation substrates, where each substrate is approximately 20 amino acid residues in length (see Example 7). It will be appreciated from this example that essentially any polypeptide with or without "post-translational modification" to amino acid sidechains can be synthesized by the method of this invention. Of course, the "post-translational modifications" (e.g., glycosylation) in the instant invention is first synthetically incorporated into the ligation substrates.

A general synthetic strategy and method is represented in FIG. 15. The first step in this method is to analyze the amino acid sequence of the peptide to be synthesized for appropriate ligation sites according to the residue preferences described in Table 1. Then, a ligation strategy is developed (see e.g. Example 7) and ligation substrates having the appropriate amino acid sequences and lengths are synthesized or obtained from recombinant or natural sources.

By way of illustration, techniques for synthesis of ligation substrates by exclusively solid-phase synthesis are set forth in *"Solid-Phase Peptide Synthesis,"* Steward & Young, (Freeman & Co., San Francisco, 1969) and U.S. Pat. No. 4,105,603, issued Aug. 8, 1978. Classical solution synthesis is described in detail in the treatise *"Methoden der Organischen Chemie(Houben-Weyl) Synthese von Peptiden,"* E. Wunsch (ed.). (1974), Georg Thieme Verlag, Stuttgard, W Ger. The fragment condensation method of synthesis is exemplified in U.S. Pat. No. 3,972,859 issued Aug. 3, 1976. Other available syntheses are exemplified by U.S. Pat. No. 3,842,067 issued Oct. 15, 1974 and U.S. Pat. No. 3,862,925 issued Jan. 28, 1975.

The ligation substrates are synthesized by any suitable method, such as, for example, by exclusively solid-phase techniques, by partial solid-phase techniques, by fragment condensation, by classical solution couplings, by recombinant DNA techniques, i.e., by fermentation of a genetically engineered host cell transformed with an expression vector containing a gene coding for the relevant polypeptide, and by a combination of both genetic engineering methods and peptide synthesis.

Referring to FIG. 15, the method comprises ligating a first and second ligation substrate with a serine protease variant, preferably the subtilisin S221C/P225A variant, hereafter "ligase". The ligation conditions are those generally described above and, more specifically, as described in Examples 3, 4, 7, and 8 below.

Generally, the first ligation substrate contains from two to about 30 amino acid residues and will have a carboxy terminus activating group (CTAG) bonded to the carboxy terminus residue and an amino terminus protecting group (ATPG) bonded to the amino terminus residue.

By carboxy terminus activating group (CTAG) as used herein is meant a group capable of activating the carboxy terminus carbonyl to nucleophilic substitution. The nucleophile in this case is the cysteine sulfur at residue 221 of the ligase. CTAG's as defined herein will be understood by those of ordinary skill to be "good leaving groups" under the conditions (i.e. aqueous solvent, pH, etc.) of the ligation reaction. Such groups are well-known and generally form esters or thioesters with the carboxy terminus carbonyl. Preferred CTAG's include 2-hydroxycarboxylic acids such as glc-amide, glc-phe-amide, glc-Phe-Gly-amide, lac-amide, lac-Leu-amide, lac-Phe-amide, and Sbz.

By amino terminus protecting group (ATPG) as used herein is meant a chemical group bonded to the a-amino terminus which is stable to the ligation conditions and thus prevents nucleophilic attack of the a-nitrogen on any electrophile such as the activated carboxy terminus carbonyl. a-amino protecting groups are well-known in the peptide synthesis art and are generally carboxylic acids or form carbamates with the amino terminus. Preferred ATPG's include: t-butyloxycarbonyl(BOC), t-amyloxycarbonyl, adamantyloxycarbonyl, p-methoxybenzyloxycarbonyl, benzyloxycarbonyl, halobenzyloxycarbonyl, p-nitrobenzyloxycarbonyl, cycloalkyloxycarbonyl, isopropyloxycarbonyl, isonicotinyl(iNOC), phenylacetic acid, and pyridine acetic acid. Most preferred ATPG's are iNOC and pyridine acetic acid.

Generally, the second ligation substrate will comprise at least two amino acid residues, preferably from two to 30 residues, and most preferably from ten to 25 residues. The carboxy terminus of the second ligation substrate may be either free, blocked, or bound to a solid matrix, i.e. resin. The amino terminus of the second ligation substrate is generally a good nucleophile, thus it will usually be a free amine, or substituted with a group or groups which do not substantially diminish the nucleophilic character of the amino terminus. Thus, a free amino terminus would include, for example, amine and lower alkyl amine terminii.

The product of the ligation step will be a first ligation product having either a free or bound carboxy terminus and an amino terminus bonded to an ATPG. This first ligation product generally will become the second ligation substrate in a subsequent ligation step and thus will require deprotection of the amino terminus. Deprotection will generally be a hydrolysis or reduction of the terminal amide bond. Deprotection conditions are generally known in the art. For example, when the ATPG is a isonicotinyl(iNOC) group, the deprotection conditions will be reduction with, for example, Zn/acetic acid or $H_2$/Pd. When, for example, the ATPG is an aromatic substituted alkylcarboxylic acid, (e.g. phenyl acetic or pyridine acetic acids), deprotection may be enzymatic with, for example, penicillin acylase (see *Methods in Enzymology*). Other deprotection conditions may include acid hydrolysis of the terminal amide.

Generally, to synthesize a longer polypeptide, i.e. one having more than 50 amino acid residues, the foregoing process will have to be repeated one or more times. When the process is repeated, the deprotected ligation product from the previous step will be the second ligation substrate in the subsequent step, and a new first ligation substrate will be obtained with its amino and carboxy terminii bonded to an ATPG and CTAG respectively. These two substrates will then be ligated with the ligase (serine protease variant) as described above. The ligation and deprotection steps are repeated until the peptide of interest is prepared.

The following is presented by way of example and is not to be construed as a limitation of the scope of the claims.

Materials and Methods

Abbreviations: DMA, dimethylacetamide; DMSO, dimethylsulfoxide; DTNB, 5,5'-dithiobis(2-nitrobenzoic acid); DTT, DL-dithiothreitol; hGH, human growth hormone; NEM, N-ethyl maleimide; PAGE, polyacrylamide gel electrophoresis; SDS, sodium dodecyl sulfate; s-Ala-Ala-Pro-Phe-pNA, N-succinyl-L-Ala-L-Ala-L-Pro-L-Phe-para-nitroanilide; s-Ala-Ala-Pro-Phe-Sbz, the thiobenzyl ester of the same succinylated peptide; TFA, trifluoroacetic acid; Tricine, N-tris(hydroxymethyl) methylglycine; Tris, tris (hydroxymethyl) aminomethane; E-Ac, acyl- or thioacyl-enzyme intermediate. Mutant proteins are designated by the wild-type residue (single-letter amino acid code) followed by their position and the mutant residue. Multiple mutants are separated by a slash. For example, S221C/P225A indicates that the serine at position 221 and the proline at position 225 have been replaced by cysteine and alanine, respectively. Protease substrate residues are designated using the nomenclature of Schechter and Berger (1967), $$NH_2-P_n \ldots P_2-P_1-C(O)-N(H)-P'_1-P'_2 \ldots P'_n-COOH$$

where the scissile peptide bond is between the $P_1$ and $P'_1$ residues.

Materials: Enzymes for DNA manipulations were from New England Biolabs or Bethesda Research Labs. Oligonucleotides were synthesized by the Organic Chemistry Department at Genentech. All peptides contain L-amino acids unless otherwise indicated, and were synthesized by standard methods (Barany and Merrifield, 1979). DL-Dithiothreitol (DTT)[1], DTNB, 2-mercapto ethanol, NEM, TFA, Tween 80, Tricine, dimethylsulfoxide, dimethylacetamide, and the substrates s-Ala-Ala-Pro-Phe-pNA and s-Ala-Ala-Pro-Phe-Sbz were from Sigma. The solvents ethanol and acetonitrile were from J. T. Baker Inc. and ammonium sulfate from ICN Biochemicals Inc. Dipeptides Ala-Phe-amide, Arg-Gly-amide, Arg-Phe-amide, Gly-Ala-amide, Gly-Leu-amide, Gly-Phe-amide, Leu-Phe-amide, Phe-Gly-amide and the tripeptide Ala-Phe-Ala-amide were obtained from BACHEM Feinchemikalien AG. The tripeptide Leu-Phe-Asp-amide was synthesized according to the general methods described in G. Barany and R. B. Merrifield (1979), in "Solid-Phase Peptide Synthesis" in the Peptides, Analysis, Synthesis Biology Special Methods i Peptide Synthesis, Part A, Vol. 2 (E. Grow, J. Meienhatter (eds.), N.Y., Academic Press), pp. 3–254. Activated thiol Sepharose as well as G-25 and G-75 Sepharose were obtained from Pharmacia LKB Technology AB.

Expression and Purification Of Variant Subtilisins: The subtilisin gene in the M13-*E. coli*- *B. subtilis* shuttle plasmid, pSS5 (Carter and Wells (1987), *Science*. 237, 398–399), was expressed in the *B. subtilis* host strain (BG2036) that is lacking its endogeneous subtilisin and neutral protease genes (Yang, M. Y., et al. (1984), *J. Bacterial*, 160, 15–21). Since maturation of subtilisin involves proteolytic removal of the prosequence (Power et al. (1986), *Proc. Natl. Acad. Sci. USA*, 83, 3096–3100), the variants with reduced protease activity were expressed in the presence of active subtilisin. This was done either by adding a small amount of purified subtilisin (to a final concentration of 500 µg/L) late in the logarithmic growth phase, or by co-culturing from an inoculum of BG2036 containing 0.1% wild type subtilisin expressing cells (Carter and Wells, (1987), supra).

The purification of inactive subtilisin variants was essentially as described (Carter and Wells (1987.), supra) except that an equal amount of cold ethanol was added to the supernatant to precipitate impurities prior to the precipitation of subtilisin by the addition of two additional volumes of cold ethanol. Furthermore, the CM-Trisacryl was substituted by SP-Trisacryl M in the ionexchange chromatography step. For the S221C mutants, the active site cysteine was utilized for purification on activated thiol Sepharose. This latter step is essential in order to separate the variant proteins from any traces of wild-type "helper" subtilisin. The equivalent step in the original procedure used a cysteine residue introduced on the surface of the protein that results in efficient removal of wild-type activity (Carter and Wells (1987), supra.; Carter and Wells (1988), *Nature*, 332, 564–568). The mutant P225A is capable of autoproteolytic processing, and therefore was cultured without helper subtilisin and was purified by standard procedures (Estell et al. (1985), *J. Biol. Chem.*, 260, 6518–6521).

Kinetic Assays. The esterase and amidase activities were obtained from initial rate measurements using a Kontron Uvikon 860 spectrophotometer. The assay for esterase activity utilized the substrate s-Ala-Ala-Pro-Phe-Sbz at (25°±0.2° C.) in 100 mM Tris-HCl (pH 8.60), 4% (v/v) dimethylsulfoxide, 0.005% (v/v) Tween 80. With the non-cysteine containing proteases, DTNB (Ellman (1959), *Arch. Biochem. Biophys.*, 82, 70–77) was added to a concentration of 37.5 µM to visualize the release of thiolbenzoate upon hydrolysis of the substrate. With the S221C derivative proteases the difference in absorbance at 250 nm between the substrate and the hydrolyzed product was used to monitor the reaction directly. The amidase activities were measured under identical conditions by following the increase in absorbance at 412 nm upon hydrolysis of p-nitroanilide from s-Ala-Ala-Pro-Phe-pNA.

Enzymatic ligation of peptides were performed at (25°±0.2)° C. in 90 mM Tricine (pH 8.0), 2% (v/v) dimethylacetamide, 0.005% (v/v) Tween 80. The comparison between substrates having different leaving groups was simplified by measuring initial reaction rates at a low substrate concentrations (70–75 µM) and at a higher concentration (1.33 mM) where rates are proportional to kcat/KM and the kcat, respectively (Fersht (1977) in Enzyme Structure and Mechanism, W. H. Freeman & Co. USA). The higher substrate concentration may still be below the KM for some of the substrates, so that values for kcat are less accurate. The aminolysis with di- and tripeptides was performed at low peptide concentrations. The aminolysis rate $V=k_{aminolysis}$ [N] [E-Ac]/KN, where [N] is the nucleophile concentration, [E-Ac] is the concentration of acyl-enzyme intermediate and KN is the dissociation constant for the binding of the nucleophile to the acyl-enzyme intermediate (Riechmann and Kasche (1985), *Biochem. Biophys. Acta.*, 830, 164–172). Since KN=[N] [E-Ac]/[N·E-Ac] a change in [N] will result in a change in [E-Ac] but at low [N], [E-Ac]>>[N·E-Ac] and $k_{aminolysis}$/KN (the apparent second order rate constants for the reaction between the different nucleophile and the acyl-enzyme intermediate) may be compared. The concentrations of the peptide nucleophiles, and the calibration of the absorbance data for the different ligation products was obtained from amino acid composition analysis. The rates of peptide ligation were measured at four or five different concentrations for each nucleophile.

Ligation reactions were analyzed by taking aliquots at different times and analyzing the peptide products by C-18 reversed phase HPLC. Peptides were eluted in a gradient of acetonitrile/0.1% TFA in water/0.1% TFA and the absorbance at 214 nm monitored. Amino acid composition analysis was used to confirm both the hydrolysis and aminolysis products and to calibrate the absorbance values. The structures of the hydrolysis and aminolysis products (using the dipeptide Ala-Phe-amide as a nucleophile) were confirmed by mass spectrometrical analysis.

Example 1

Production of Subtilisin Variants

Molecular modeling was performed on an Evans and Sutherland PS300 using the program FRODO (Jones (1978), *J. App. Crystallogr*, 11, 268–272) and coordinates from a 1.8 Å resolution structure of subtilisin BPN' from *Bacillus amyloliquefaciens* (Bott et al. (1988), *J. Biol. Chem.*, 263, 7895–7906). The S221C mutation was introduced (Carter et al. (1986), *Nucl. Acids Res.*, 13, 4431–4443)) into the wild-type subtilisin gene (Wells et al. (1983), *Nucl. Acids Res.*, 11, 7911–7925) using the oligonucleotide 5'-ACAAC GGTACCTGCATGGCATCTCC (asterisks indicate the positions of altered nucleotides and underlined is a unique KpnI site). The S221C/P225A mutations were introduced into the S221C template using the oligonucleotide 5'- GCG-TACAACGGTACTGCATGGCA TCTCGCACGTTGCC (asterisks indicate altered nucleotides and underlined is a new FspI site) by restriction-selection against the KpnI site (Wells et al. (1986), *Phil. Trans. R. Soc. Lond.*, A317, 415–423). The construction of the mutants G166E and E156Q/G166K was described by Wells et al. (1987), *Proc. Natl. Acad. Sci. USA*, 84, 1219–1223, and the mutant G166I by Estell et al. (1986), *Science*, 223, 659–663. Combinations of the mutations around the active site (positions 221 and 225) and around the P1 binding pocket (156 and 166) were obtained by ligation of mutated restriction fragments split by the enzyme PpuMI. See EPO Publication No. 0 251 446, published Jan. 9, 1988. All mutants were verified by dideoxy sequencing (Sanger et al. (1977), *Proc. Natl. Acad. Sci. USA*, 83, 3096–3100). The mutated gene encoding P225A mutant was a kind gift from T. Graycar (Genencor, S. San Francisco, Calif.). It was synthesized by primer extension mutagenesis on a single stranded M13 subclone of *Bacillus amyloliquefaciens* subtilisin using the mutagenic oligonucleotides depicted in FIG. 13.

The above identified subtilisin variants were used in conjunction with the ligation substrates disclosed in Example 2 and Example 3 to provide the previously discussed results.

Example 2

Synthesis of FPTIPAAPF-glycolate-F-amide

The synthesis of a C- terminal amide ligation peptide is accomplished by attachment of the first Boc protected amino acid (Boc-Phenylalanine) to 4-methylbenzhydrylamine resin (Bachem L. A.) using diisopropylcarbodiiimide in methylenechloride. Standard Boc synthetic protocols for the synthesis of the protected peptide are followed. Barany, G., et al. (1979), in "Solid-Phase Peptide Synthesis", in *The Peptides, Analysis, Synthesis, Biology. Special Methods in Peptide Synthesis*, Part A. Vol. 2 (E. Grow, J. Meienhoffer (eds), New York Academic Press), pp. 3–254. The glycolic acid residue was incorporated as the corresponding t-butyl ether. Removal of the t-butyl ether with 50% trifluoroacetic acid in methylene chloride and coupling of the subsequent amino acid with diisopropylcarbodiimide and 10 mol % dimethylaminopyridine in 90% methylene chloride, 10% dimethylacetamide, afforded the ester linkage. Subsequent amino acids were incorporated again using standard Boc protocols. The crude peptide was deprotected and removed from the resin with hydrogen fluoride. The crude peptide was then purified by reverse phase HPLC. Purity was determined by mass spectral analysis. M+1 calc. 1164.5, $M^{+1}$ obs. 1164.6. Similar methods are used to produce other first ligation peptides.

Example 3

Growth Hormone Expression and Semi-Synthesis

The truncated form of human growth hormone (des-octa hGH containing residues 9–191) was expressed in *E. coli* W3110 (tonA; ATCC27325) using the *E. coli* alkaline phosphatase promoter and the signal peptide from *E. coli* heat-stable enterotoxin II (Chang et al. (1987), *Gene*, 55, 189–196). Cell paste was resuspended in four volumes of 10 mM Tris HCl, pH 8.0, to release the hGH from the periplasmic space. The cells were pelleted and the hGH was purified from the supernatant (Olson et al. (1981), *Nature*, 293. 408–411).

Peptides derived from the amino-terminal sequence of hGH having the sequence FPTIPLSR or FPTIPAAPF on their carboxyl-termini were esterified with the leaving group glycolate-Phe-amide. The reaction between des-octa hGH (0.5 mM) and either of the two peptide substrates (2.4 mM final) was performed in Tricine (pH 8.0) at 20° C. using either S221C/P225A or G166E/S221C/P225A subtilisin at final concentrations of 3.0 µM or 3.4 µM, respectively. The reaction was stopped by mixing an aliquot with an equal volume of 100 mM NEM (which alkylates the active site cysteine). Loading buffer (5% 2-mercaptoethanol, 5% glycerol, 10 mM Tris HCl pH 8.0, 1 mM EDTA, 0.25% SDS, final concentrations) was added and the samples were boiled and analyzed by SDS-PAGE (Laemmli (1970), *Nature*, 227. 680–685). See FIG. 12. The ligation products were blotted onto polyvinylidene difluoride membranes (Matsudaira et al. (1987), *J. Biol. Chem.*, 262, 10035–10038) and the amino-terminal sequences were determined.

Example 4

Modification of Protropin with Peptides

In addition to ligating peptides to form larger proteins, Protropin (met-hGH) has also been modified with the S221C/P225A peptide ligase. One of the peptides used in the growth hormone semi-synthesis, FPTIPAAPF-glycolyl-F-amide, was used in these ligations. Protropin (75 µM) was reacted with the peptide (350 µM to 7 mM) in the presence of 3 µM of the ligase in 115 µl of the reaction buffer (10 mM Tricine, pH 8.0) at 25° C. The progress of the ligation reaction was monitored by mixing an aliquot (15 µl) with an equal volume of 100 mM NEM at time intervals between 1 minute and 1 hour. The samples were then run on a SDS-PAGE gel (Laemmli *Nature* 227, 680–685 (1970)). FIG. 15 shows that most of the substrate is ligated after an hour, as shown by the appearance of a product of expected molecular weight.

Example 5

Confirmation of Ligase Substrate Specificity

To demonstrate that the ligase substrate specificity is similar to the substrate specificity for the hydrolysis of peptides for subtilisin, several different ligations were tried. The substrates used and the results obtained confirm that ligation is restricted to ligation substrates that have amino acid sequences similar to the sequence of subtilisin hydrolysis substrates.

The presence of proline at either the P1 or P2' position has been shown to inhibit subtilisin hydrolase activity. Carter et al. Proteins, Structure, Function and Genetics, vol. 6. p240–248 (1989). hGH has a proline at the P2' position while the des-1 hGH has a proline at the P1' position. Accordingly, substitution of Protropin with either hGH or des-1 hGH in the experimental conditions of Example 4 resulted in no ligation (data not shown).

This result was verified using insulin-like growth factor-1 (IGF-1). The N-terminal sequence of IGF-1 is GPETLC. This proline at position P2' was expected to prevent ligation, similar to hGH. The substitution of IGF-1 for Protropin in the Example 4 experimental conditions resulted in no ligation (data not shown).

These results indicate that the N-terminal sequences of the peptides to be ligated are important, just as they are for the corresponding sequence in hydrolysis reactions with the wild-type subtilisin.

Example 6

Specificity is Further Defined by the N-terminus

A further level of substrate specificity is obtained due to the importance of conformation of the N-terminus of the substrate. In addition to the amino acid sequence, the N-terminal structure of one of the pair of a prospective substrates is important. Subtilisin has been shown to prefer an extended conformation of the amino acids at the cleavage site. Several acceptor proteins that possess favorable amino acids sequence failed to be ligated or were ligated in only modest amounts, or required special treatment for ligation to occur, suggesting that these substrates lack the necessary extended conformation at the N-terminus.

The potential importance of conformation and N-terminal flexibility was demonstrated using IGF-1. Two modified forms of IGF-1 were used. The IGF-1 from brain has 3 residues from the amino terminus removed. This form of the protein, des-3 IGF-1, no longer has a proline at the P2' position. Under Example 4 conditions, no ligation of either peptide was seen to des-3 IGF-1 under these non-reducing conditions. However, by pretreating the substrate with reducing agent (10 mM DTT) for 1 hour, ligation was observed (5%). Another peptide, Long Arg-3 IGF-1, has the first 13 amino acid residues of porcine growth hormone (MFPAMPLSSLFVN) attached to the Glu3Arg variant of IGF-1. The high N-terminal sequence homology of this protein to Protropin would suggest it can be used as a substrate. Under Example 4 conditions with the addition of pretreatment with 10 mM DTT for an hour, some ligation (≈5%) was observed. By adding 0.1% SDS and 10% DMSO, and carrying out the reaction at 50° C., the amount of product was increased 2 to 3-fold (data not shown).

Using the hGH receptor in place of Protropin under Example 4 experimental conditions resulted in no ligation, even after 5 hours with a 4 fold higher concentration of the ligase (data not shown). While the hGH receptor has the N-terminal sequence FSGSEAT and thus the sequence conforms to acceptable subtilisin substrate primary sequence, the lack of ligation is attributed to either the lack of accessibility of the N-terminus or a highly structured N-terminus.

A similar result was obtained for Relaxin. Relaxin consists of two chains, A and B. The A chain has a pyroglutamate at the N-terminus, so the a-amine is incapable of acting as a nucleophile. In constrast, the B-chain has the sequence DSWM and should be a suitable substrate in the presence of high salt. However, modification of the Example 7 experimental conditions to include 2M NaCl in the buffer solution resulted in no ligation after an hour (data not shown).

These results demonstrate that by judicious selection of reaction conditions (including temperature, detergents, pH and non-aqueous solvents), it should be possible to selectively alter the conformation of the N-terminal segment of the substrate protein while retaining the ligase activity, thus allowing highly specific ligations to occur.

Example 7

Use of Subtiligase to Synthesize Wild Type Ribonuclease A

The total synthesis of ribonuclease A was undertaken to demonstate the Utility of using the ligase for protein synthesis via sequential ligation of synthetic peptide fragments. Ribonuclease A, a 124 residue protein, was subdivided into six synthetically accessible peptide fragments shown in FIG. 16 based on the known sequence specificity of the ligase. C-terminal glycolate-F-amide activated peptide substrates were prepared as described in Example 2. Prior to cleavage from the solid phase resin, the N-termini of the substrates were protected using isonicotinyl p-nitrophenyl carbonate (Veber et al. (1977), *J. Org. Chem.*, 42, 3286–3288) to prevent self ligation during enzymatic coupling. The isonicotinyl (iNoc) protecting group (FIG. 16) was chosen because of its stability to conditions used for cleavage from the solid phase resins (anhydrous HF) and its ease of removal under reductive conditions (Zn/acetic acid, or $H_2$/Pd).

A typical ligation reaction consists of adding 0.1 mL of iNoc protected glycolate activated peptide (10 mM in dimethylacetamide) to 0.2 mM substrate in 1 mL of 100 mM tricine buffer pH 8. Subtiligase is then added to a final concentration of 10 mM and the mixture allowed to stand 12 h at 25° C. The ligation product is isolated by reverse phase C18 preparative HPLC ($CH_3CN/H_2O$ gradient), lyophilized and analyzed by mass spectral analysis. The resulting peptide (2–5 mg) is dissolved in 2 mL of 50% aqueous acetic acid and 10 mg of HCl activated zinc dust is added (Tseuda et al. (1963), *J. Org. Chem.*, 28, 783–785) and the solution stirred 3 h at 25° C. The deprotected peptide is isolated by reverse phase C18 preparative HPLC ($CH_3CN/H_2O$ gradient), lyophilized and analyzed by mass spectral analysis. The ligation and deprotection process is then repeated sequentially with the remaining iNoc protected glycolate-F-amide activated peptides to yield wild type ribonuclease A (FIG. 16). This process could be applied to the synthesis of virtually any protein and could be used to incorporate non-natural amino acids or even non-peptide molecules such as steroids, catalytic cofactors, and polysaccharides.

Example 8

Use of Subtiligase to Introduce Unnatural Amino Acids into Ribonuclease

Digestion of ribonuclease A with wt subtilisin yields two fragments consisting of residues 1–20 (S-peptide) and residues 21–124 (S-protein). Several glycolate-F-amide activated S-peptide analogs (peptides containing unnatural amino acids have been synthesized and ligated to the N-terminus of S-protein to yield ribonuclease A containing non-natural amino acids. Such amino acid substitutions would not be possible using conventional mutagenesis on recombinant protein. Peptides 1 and 2. shown in FIG. 17 were designed to improve the stability of ribonuclease A and to incorporate heavy atoms for crystalographic studies.

A typical ligation involves adding a 10x stock solution of the S-peptide analog (10 mM in dimethylacetamide) to S-protein (2 mg/mL in 100 mM tricine, pH 8) followed by ligase to a final concentration of 10 mM. The reaction is allowed to proceed overnight at 25° C. and quenched by the addition of an equal volume of 100 mM N-ethylmaleimide. The reactions can be monitored by SDS polyacrylamide gel electrophoresis (16% acrylamide) (Laemmli (1970), Nature, 227, 680–685) and proceed to >80% completion under these conditions. The products are purified by size exclusion chromatograhy (Sephadex G-50) or by preparative C18 HPLC.

Having described the preferred embodiments of the present invention, it will appear to those of ordinary skill in the art that various modifications may be made and that such modifications are intended to be within the scope of the present invention.

All references are expressly incorporated herein by reference.

What is claimed is:

1. A first ligation substrate capable of specifically binding to a serine protease variant having peptide ligase activity and catalytically reacting with a second ligation substrate to form a ligation product, said first ligation substrate comprising at least one amino acid residue having its carboxy-terminus esterified with a 2-hydroxy carboxylic acid and said serine protease variant having a catalytic triad consisting of aspartate, histidine and serine.

2. The first ligation substrate of claim 1 wherein said 2-hydroxy carboxylic acid is glycolate or lactate.

3. The first ligation substrate of claim 2 wherein said 2-hydroxy carboxylic acid is glycolate.

4. The ligation substrate of claim 1, wherein said serine protease variant is a subtilisin variant.

5. A first ligation substrate capable of specifically binding to a serine protease variant having peptide ligase activity and catalytically reacting with a second ligation substrate to form a ligation product, said first ligation substrate comprising at least one amino acid residue having its carboxy-terminus esterified with a 2-hydroxy amide and said serine protease variant having a catalytic triad consisting of aspartate, histidine and serine.

6. The ligation substrate of claim 5, wherein said serine protease variant is a subtilisin variant.

7. The first ligation substrate of claim 1 or 5 further comprising a second amino acid residue selected from the group consisting of phenylalanine, tyrosine, tryptophan, leucine, and methionine.

8. Composition comprising 1) a serine protease variant having peptide ligase activity and a catalytic triad consisting of aspartate, histidine and serine, and 2) the first ligation substrate of claim 1 or 5.

9. The composition of claim 8, wherein said serine protease variant is a subtilisin variant.

10. The first ligation substrate of claim 1 or 5 wherein said amino acid residue is a naturally occurring amino acid.

11. The first ligation substrate of claim 1 or 5 wherein said amino acid residue is a non-naturally occurring amino acid.

12. The first ligation substrate of claim 1 or 5 wherein said amino acid residue is a large hydrophobic amino acid or analog.

* * * * *

UNITED STATES PATENT AND TRADEMARK OFFICE
CERTIFICATE OF CORRECTION

PATENT NO. : 5,736,512

DATED : April 7, 1998

INVENTOR(S) : ABRAHMSEN et al.

It is certified that error appears in the above-identified patent and that said Letters Patent is hereby corrected as shown below:

Column 16, about line 21, table III, under "KM" column, delete "$(5.5 \pm 0.3) \times 10^4$" and insert therefor --$(5.5 \pm 0.1) \times 10^{-5}$--.

Column 16, about line 21, table III, under "kcat/MM" column, delete "$9.3 \times 10^3$" and insert therefor --$(2.5 \pm 0.3) \times 10^4$--.

Column 16, about line 21, table III, under "hydrolase" column, in the blank space beneath "$1.6 \times 10^{-3}$" insert --$3.0 \times 10^2$--.

Column 20, line 53 and 54, delete the new parapgraphin so that line 53 reads --the CM--.

Column 21, line 5, delete "$(25° \pm 0.2°$ C.)" and insert therefor --$(25 \pm 0.2°$ C.)--.

Column 21, line 18, delete "$(25° \pm 0.2)°$ C." and insert therefor --$(25 \pm 0.2)°C$--.

Signed and Sealed this

Eleventh Day of August 1998

Attest:

BRUCE LEHMAN

*Attesting Officer*     *Commissioner of Patents and Trademarks*